(12) United States Patent
Bunner et al.

(10) Patent No.: US 9,496,125 B2
(45) Date of Patent: Nov. 15, 2016

(54) INTERFACING WITH A DIGITAL MICROFLUIDIC DEVICE

(75) Inventors: Bernard Bunner, Cambridge, MA (US); Geoff C. Gerhardt, Millbury, MA (US); Joseph A. Jarrell, Newton Highlands, MA (US)

(73) Assignee: Waters Technologies Corporation, Milford, MA (US)

( * ) Notice: Subject to any disclaimer, the term of this patent is extended or adjusted under 35 U.S.C. 154(b) by 1033 days.

(21) Appl. No.: 12/919,570

(22) PCT Filed: Mar. 3, 2009

(86) PCT No.: PCT/US2009/035811
§ 371 (c)(1),
(2), (4) Date: Jan. 24, 2011

(87) PCT Pub. No.: WO2009/111431
PCT Pub. Date: Sep. 11, 2009

(65) Prior Publication Data
US 2011/0107822 A1    May 12, 2011

Related U.S. Application Data

(60) Provisional application No. 61/033,586, filed on Mar. 4, 2008.

(51) Int. Cl.
*H01J 49/00*   (2006.01)
*H01J 49/16*   (2006.01)
*B01L 3/00*    (2006.01)
*B03C 5/02*    (2006.01)
(Continued)

(52) U.S. Cl.
CPC ........ *H01J 49/167* (2013.01); *B01L 3/502792* (2013.01); *B03C 5/024* (2013.01);
(Continued)

(58) Field of Classification Search
CPC .... B05B 5/025; B05B 5/0255; H01J 49/167; H01J 49/0018; G01N 27/44717; G01N 30/6095; B01D 11/04976; B01D 11/04; B01L 2300/0819; B01L 2300/089; B01L 3/502792; B01L 3/502707; B01L 3/502715; B01L 3/0268
USPC ........ 204/600, 660, 663; 347/54, 58, 74–78, 347/81, 55
See application file for complete search history.

(56) References Cited

U.S. PATENT DOCUMENTS 4,531,056 A    7/1985    Labowsky et al.
6,110,343 A    8/2000    Ramsey et al.
(Continued)

FOREIGN PATENT DOCUMENTS

WO    03057010      7/2003
WO    2006026351    3/2006

OTHER PUBLICATIONS

Sung et al., Electrophoresis, 2005, 26, 1783-1791.*
(Continued)

*Primary Examiner* — Gupreet Kaur
(74) *Attorney, Agent, or Firm* — Muirhead and Saturnelli, LLC

(57) ABSTRACT

Described are techniques for use in connection with analyzing a droplet. One or more droplets of a sample are formed on a surface of a digital microfluidic device. The droplets are manipulated to perform processing using said one or more droplets generating one or more resulting droplets. The one or more resulting droplets may be transferred from the microfluidic device to another device for analysis. The one or more droplets may also be provided to the digital microfluidic device from yet another device or analysis instrument.

13 Claims, 15 Drawing Sheets

(51) Int. Cl.
*G01N 30/06* (2006.01)
*G01N 30/20* (2006.01)
*B01L 3/02* (2006.01)

(52) U.S. Cl.
CPC ............ *G01N 30/06* (2013.01); *G01N 30/20* (2013.01); *B01L 3/0268* (2013.01); *B01L 2200/026* (2013.01); *B01L 2300/089* (2013.01); *B01L 2300/0819* (2013.01); *B01L 2400/0427* (2013.01); *B03C 2201/26* (2013.01); *G01N 2030/201* (2013.01)

(56) References Cited

U.S. PATENT DOCUMENTS

| | | | |
|---|---|---|---|
| 6,337,480 | B1 | 1/2002 | Andrien et al. |
| 6,911,132 | B2 | 6/2005 | Pamula et al. |
| 7,147,763 | B2 | 12/2006 | Elrod et al. |
| 7,178,386 | B1* | 2/2007 | Gamble et al. .............. 73/61.57 |
| 7,303,727 | B1* | 12/2007 | Dubrow ............. G01N 30/6095 422/50 |
| 2005/0047969 | A1* | 3/2005 | Zhao et al. ................... 422/100 |
| 2006/0060769 | A1 | 3/2006 | Bousse et al. |
| 2006/0114296 | A1 | 6/2006 | Gascoyne et al. |
| 2006/0193748 | A1* | 8/2006 | Tai et al. .......................... 422/70 |
| 2006/0194331 | A1 | 8/2006 | Pamula et al. |
| 2006/0231398 | A1* | 10/2006 | Sarrut et al. ................... 204/450 |
| 2007/0128078 | A1* | 6/2007 | Sarrut et al. ................... 422/99 |
| 2007/0242111 | A1 | 10/2007 | Pamula et al. |
| 2009/0008253 | A1* | 1/2009 | Gilbert et al. ................ 204/453 |

OTHER PUBLICATIONS

Davis et al., Anal. Chem, 1995, 4549-4556.*
Pinto et al., Electrophoresis, 2000, 21, 181-190.*
Figeys et al., Nature Biotechnolgoy, 1996, 1579-1583.*
Torkkeli, Altti et al: "Droplet Manipulation on a Superhydrophobic Surface for Microchemical Analysis"; The 11th International Conference on Solid-State Sensors and Actuators, Munich, Germany, Jun. 10-14, 2001.
Dubois, Philippe et al: "Ionic Liquid Droplet as e-Microreactor", Anal. Chem., Jul. 16, 2006, vol. 78, No. 14, 4909-4917.
Lee, Junghoon et al.: "Addressable Micro Liquid Handling by Electric Control of Surface Tension"; Department of Mechanical Engineering, Northwestern University, Evanston, Illinois 60208-3111.
Torkkeli, Altti et al.: "Electrostatic Transportation of Water Droplets on Superhydrophobic Surfaces"; University of Turku, Department of Biotechnology, Tykistokatu 6A, FIN-20520 Turku, Finland.
Srinivasan, Vijay et al.: "An integrated digital microfluidic lab-on-a-chip for clinical diagnostics on human physiological fluid"; Journal of the Royal Society of Chemistry 2004, Lab Chip, 2004, 4, 310-315.
Ren, H. et al.: "Automated on-chip droplet dispensing with volume control by electro-wetting actuation and capacitance metering"; Science Direct, Sensors and Actuators B 98 (2004) 319-327.
Dole, Malcolm et al.: "Molecular Beams of Macroions"; The Journal of Chemical Physics, vol. 49, No. 5, pp. 2240-2249.
European Search Report for Application No. EP09717790, dated Aug. 23, 2011, cf Form 1507.
PCT International Search Report for Application No. PCT/US09/35811, dated May 4, 2009, form PCT/ISA/210.
PCT International Written Opinion or Application No. PCT/US09/35811, dated May 4, 2009, form PCT/ISA/237.
Torkkeli, et al., "Droplet Manipulation on a Superhydrophobic Surface for Microchemical Analysis," VTT Technical Research Centre of Finland, Transducers '01, Eurosensors XV, Jun. 10-14, 2001.

* cited by examiner

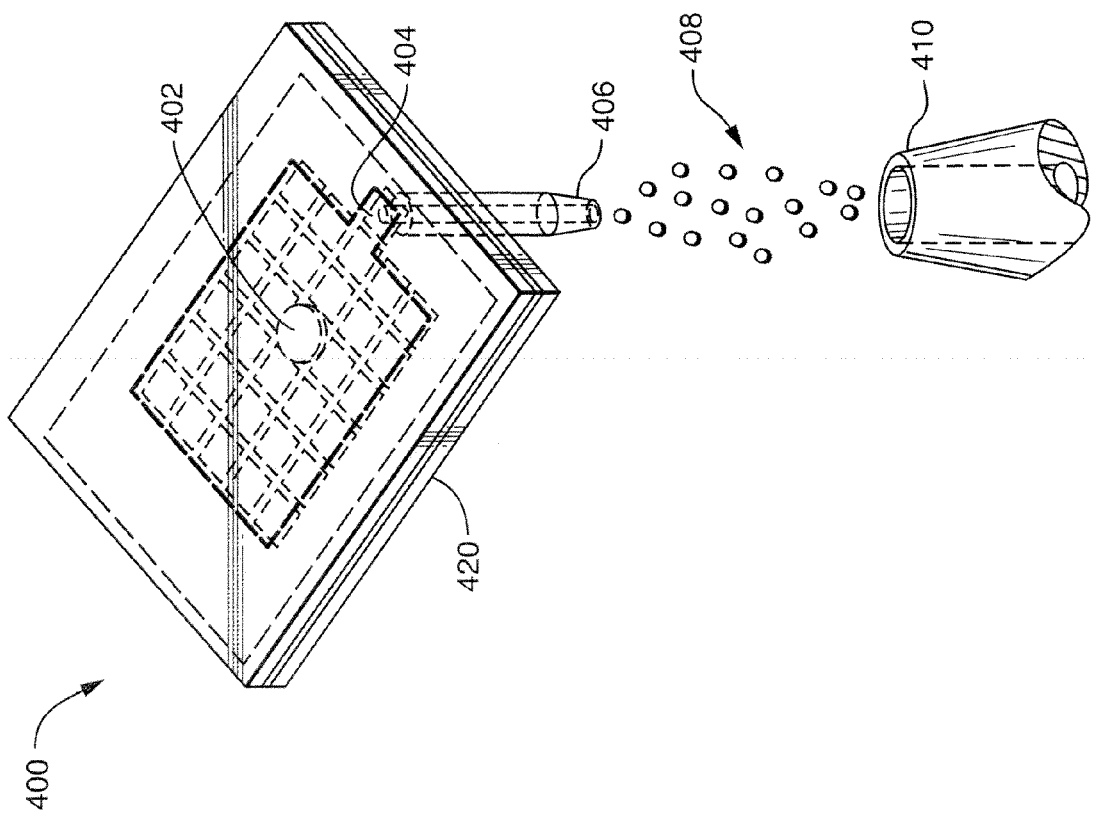

INTERFACING WITH A DIGITAL MICROFLUIDIC DEVICE

CROSS REFERENCE TO RELATED APPLICATIONS

This application is the National Stage of International Application No. PCT/GB2009/000071, filed Jan. 12, 2009, which claims priority to and benefit of U.S. Provisional Patent Application Ser. No. 61/033,586, filed 4 Mar. 2008. The entire contents of these applications are incorporated herein by reference.

TECHNICAL FIELD

This application generally relates to techniques for use with a digital microfluidic device (DMD), and more particularly interfacing an instrument or other device with a DMD.

DESCRIPTION OF RELATED ART

Liquid samples may be processed in a laboratory or other environment for a variety of different purposes and applications. Microfluidics may be characterized as the behavior, control and manipulation of fluids that are geometrically limited to a small scale. Continuous-flow microfluidics technologies are based on manipulation of continuous liquid flow through a channel. As an alternative to a continuous flow microfluidics, digital or droplet-based microfluidic techniques provide for manipulation of discrete and small volumes of liquids in the form of droplets. The foregoing may be referred to as digital microfluidics because it operates on discrete volumes of fluids that can be manipulated by binary electrical signals. By using discrete unit-volume droplets, a microfluidic operation may be defined as a set of repeated basic operations, i.e., moving one unit of fluid over one unit of distance. Droplets may be formed using surface tension properties of the liquid. Actuation of a droplet is based on the presence of electrostatic forces generated by electrodes placed beneath the bottom surface on which the droplet is located. Different types of electrostatic forces can be used to control the shape and motion of the droplets. One technique that can be used to create the foregoing electrostatic forces is based on dielectrophoresis which relies on the difference of electrical permittivities between the droplet and surrounding medium and may utilize high-frequency AC electric fields. Another technique that can be used to create the foregoing electrostatic forces is based on electrowetting which relies on the dependence of the contact angle of the droplet on voltage and may utilize DC or low-frequency AC field.

Electrowetting has been used in connection with implementation of a digital microfluidic device (DMD). With such a DMD, droplets are placed on a surface having electrodes located beneath the surface. The shape and motion of the droplets may be controlled by switching the voltages of the electrodes. By sequentially energizing and de-energizing the electrodes in a controlled manner, one or more droplets can be moved along a path or array formation of electrodes. Detection or analysis related to processing of one or more droplets using the DMD is performed "on-chip" (that is on the DMD itself), such as using "on-chip" electrical and/or optical detection. One such technique that may be used is laser induced fluorescence (LIF) in which a droplet is moved to a location on the DMD and a laser beam is directed onto the droplet causing optical emissions from molecules that have been excited to higher energy levels by absorption of electromagnetic radiation. Emission of fluorescent light therefrom may be used to detect whether a particular reaction occurred.

SUMMARY OF THE INVENTION

In accordance with one aspect of the invention is a method of analyzing a droplet comprising: forming one or more droplets of a sample on a surface of a digital microfluidic device; manipulating said one or more droplets to perform processing using said one or more droplets generating one or more resulting droplets; and transferring said one or more resulting droplets from said digital microfluidic device to another device for analysis. The another device may perform mass spectrometry. The another device may perform liquid chromatography. The step of manipulating may be performed by controlling voltages associated with different control electrodes located in a bottom portion of said microfluidic device and said one or more droplets may be located on a surface of said bottom portion over said control electrodes. The digital microfluidic device may contain a tip portion, and the step of transferring may include: moving a droplet to an end of said tip portion; and creating an electrical field between said digital microfluidic device and an inlet of said another device, said electrical field being sufficient to cause formation of a Taylor cone and electrospray ionization of said droplet. The tip portion of said digital microfluidic device may include one of said control electrodes located in a section of said bottom portion and said droplet may be moved to said tip portion from another location adjacent to said tip portion by setting voltages for each of said one control electrode in said tip portion and one or more other control electrodes associated with said another location in accordance with electrowetting principles. The digital microfluidic device may include a top portion and said one or more droplets may be positioned on a surface of said bottom portion and between said top portion and said bottom portion. The top portion may include a reference electrode, and said reference electrode may be covered with an insulation layer or coating except for a region of said reference electrode that is exposed toward the end of said tip portion. The digital microfluidic device may include a top portion and said one or more droplets may be positioned on a surface of said bottom portion and between said top portion and said bottom portion, said top portion including a reference electrode with reference electrode being covered with an insulation layer or coating that is one of hydrophobic and electrically conducting or hydrophobic and electrically insulating. The insulation layer or coating may be hydrophobic and electrically insulating, and an external electrically conductive coating may be provided at the tip portion to provide for electrical contact with a droplet in said tip portion in connection with generation of an electric field between said droplet and an inlet of said another device. The tip portion may include a gap layer formed between said top portion and said bottom portion wherein droplets are located and wherein sides of said tip portion are not enclosed at said gap layer. The tip portion may include a gap layer formed between said top portion and said bottom portion wherein droplets are located and wherein sides of said tip portion are partially enclosed at said gap layer by forming sidewalls from edges of said digital microfluidic device extending to a location in said tip portion prior to said end of said tip portion. The tip portion of said digital microfluidic device may not include one of said control electrodes located in a section of said bottom portion, and said digital microfluidic device may include a top portion. The one or more droplets may be positioned on a surface of said bottom portion and between said top portion and said bottom portion, and the surface of said bottom portion and a surface of said top portion facing said one or more droplets may each include a hydrophilic surface. The tip portion may include a reference electrode in said top portion in which said reference electrode is at least partially exposed making electrical contact with a droplet in said tip portion. The surface of said top portion facing said one or more droplets may be hydrophilic and electrically conducting. The top portion may not include a reference electrode and an external electrically conductive coating may be provided at the tip portion to provide for electrical contact with a droplet in said tip portion in connection with generation of an electric field between said droplet and an inlet of said another device. The tip portion may include a gap layer formed between said top portion and said bottom portion wherein droplets are located and wherein sides of said tip portion are not enclosed at said gap layer. The tip portion may include a gap layer formed between said top portion and said bottom portion wherein droplets are located and wherein sides of said tip portion are partially enclosed at said gap layer by forming sidewalls from edges of said digital microfluidic device extending to a location in said tip portion prior to said end of said tip portion. The digital microfluidic device may be coupled to a tube that is perpendicular to a plane containing said digital microfluidic device. The tube may be connected to said bottom portion of said digital microfluidic device, and the method may include applying a first voltage at a first control electrode in said bottom portion causing a droplet to move to a location over said first control electrode at which said tube is connected, said droplet moving from said location on said digital microfluidic device through a hole in said bottom portion at said location, said droplet flowing through said tube to a tip of said tube containing an opening therein. The method may also include creating an electrical field by applying a voltage to a control electrode in said bottom portion of said digital microfluidic device, said electrical field being sufficient to cause formation of a Taylor cone at said tip of said tube and electrospray ionization of droplets emitted from said tip directed to an inlet of said another device. The tube may have an inner hydrophilic surface. The tube may be made of an electrically conductive material and an electric field may be created by applying a voltage to said tube wherein said electrical field is sufficient to cause formation of a Taylor cone at said tip of said tube and electrospray ionization of droplets emitted from said tip directed to an inlet of said another device. The tube may be made of a material which is not electrically conductive, and at least a tip portion of the tube may be coated with an electrically conductive material. An electric field may be created by applying a voltage to said electrically conductive material wherein said electrical field is sufficient to cause formation of a Taylor cone at said tip of said tube and electrospray ionization of droplets emitted from said tip directed to an inlet of said another device. The other device may be coupled to said digital microfluidic device using a fitting that is in a same plane as said digital microfluidic device. The fitting may be coupled to a tube and a droplet may be transported to a location on a surface of said bottom portion over a control electrode. Negative pressure may be applied at a pump of said other device resulting in said droplet being aspired from said digital microfluidic device, through said fitting and said tube to a port of an injection valve of said other device. The other device may be coupled to said digital microfluidic device using a fitting that is in a different plane than a plane of said digital microfluidic device. The fitting may be perpendicular to said plane of said digital microfluidic device. The step of manipulating may include processing to perform a chemical reaction. The other device may include one of a capillary electrophoresis device, a photospectrometer or other type of spectrometer. The method may also include providing said one or more droplets of a sample used on the surface of a digital microfluidic device from an analysis instrument. The analysis instrument may be a liquid chromatographic instrument.

In accordance with another aspect of the invention is a system comprising; a digital microfluidic device including a bottom portion with one or more control electrodes formed thereon used to manipulate a droplet formed on a surface over said one or more control electrodes; means for providing one or more droplets of a fluid to said digital microfluidic device; means for manipulating said one or more droplets to perform processing using said one or more droplets generating one or more resulting droplets; and means for transferring said one or more resulting droplets from said digital microfluidic device to another device for analysis. The digital microfluidic device may include a top portion with a reference electrode located therein. The bottom portion of said digital microfluidic device may include a reference electrode located therein. The another device may be used to perform mass spectrometry. The another device may be used to perform liquid chromatography. The means for providing one or more droplets of a fluid to said digital microfluidic device may include an analysis instrument. The analysis instrument may be a liquid chromatographic instrument. The system may also include a computer readable medium comprising code stored thereon for providing instructions controlling application of one or more voltages, said one or more voltages being used to one or more control electrodes to facilitate movement of one or more droplets on said digital microfluidic device; and a processor for executing instructions stored on said computer readable medium. The computer readable medium may further comprise code stored thereon for one or more of: controlling said other device, providing said one or more droplets of a fluid to said digital microfluidic device, manipulating said one or more droplets to perform processing using said one or more droplets generating one or more resulting droplets, and transferring said one or more resulting droplets from said digital microfluidic device to another device for analysis.

In accordance with yet another aspect of the invention is a system comprising: an analysis instrument that performs an analysis of a sample; a digital microfluidic device including a bottom portion with one or more control electrodes formed thereon used to manipulate a droplet formed on a surface over said one or more control electrodes; and means for providing one or more droplets of said sample from said analysis instrument to said digital microfluidic device. The analysis instrument may perform liquid chromatography on said sample.

BRIEF DESCRIPTION OF THE DRAWINGS

Features and advantages of the present invention will become more apparent from the following detailed description of exemplary embodiments thereof taken in conjunction with the accompanying drawings in which:

FIG. 4 is an example of another embodiment of the system of FIG. 1 including an analysis instrument that performs mass spectrometry;

DETAILED DESCRIPTION OF EMBODIMENT(S)

Figure 1:
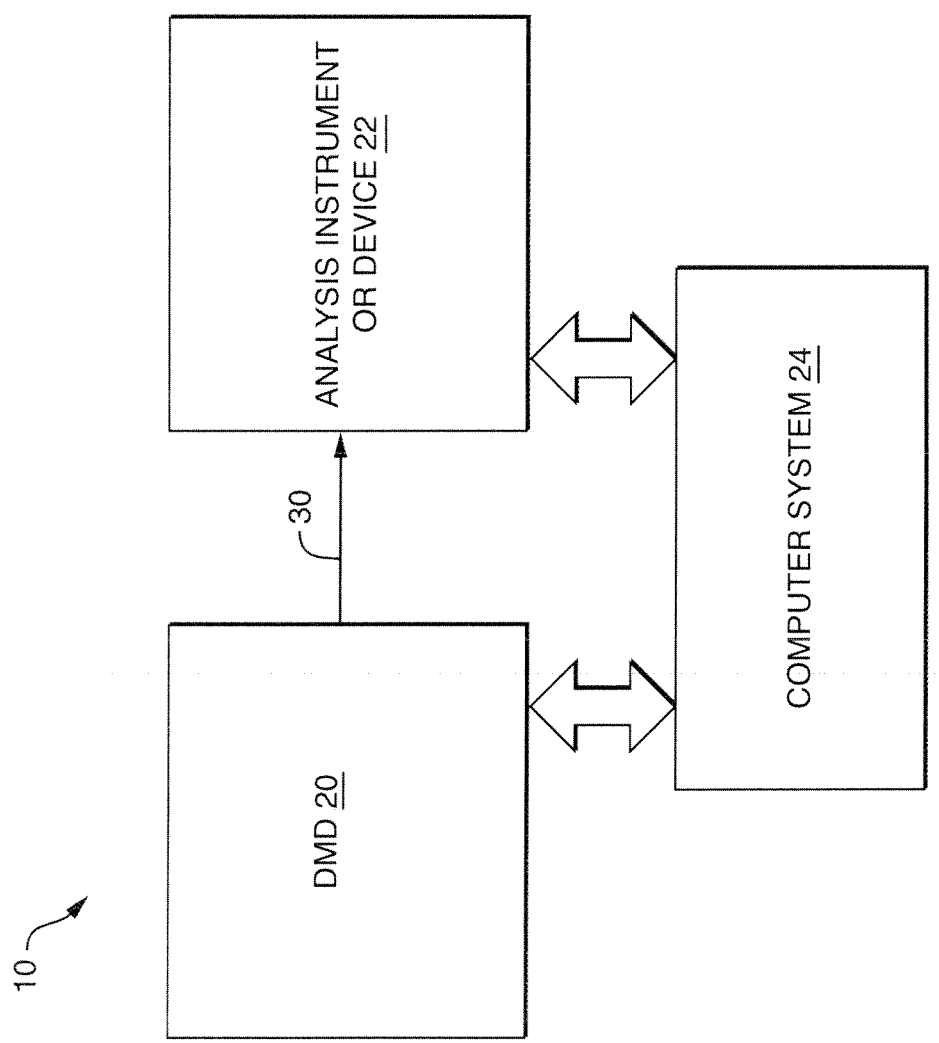
FIG. 1 is an example of an embodiment of a system in accordance with the techniques described herein.

Referring to FIG. 1, shown is an example of an embodiment of a system in accordance with the techniques described herein. The system 10 includes a digital microfluidic device (DMD) 20, an analysis instrument or device 22 and a computer system 24. As will be described in more detail below, element 30 represents the transfer of fluid contained in one or more droplets from the DMD 20 to the analysis instrument or device 22. Described herein are techniques that may be used in connection with interfacing the DMD 20 with the analysis instrument or device 22 to facilitate the transfer of one or more droplets from the DMD 20 to the analysis instrument or device 22 where the one or more droplets may be further analyzed.

The DMD 20 is a device that utilizes digital or droplet-based microfluidic techniques to provide for manipulation of discrete and small volumes of liquids in the form of droplets. The foregoing may be referred to as digital microfluidics because it operates on discrete volumes of fluids that can be manipulated by binary electrical signals. The droplets may be characterized as small scale, such as, for example, in the range of 10 nl to 10 µl in size. By using discrete unit-volume droplets, a microfluidic operation may be defined as a set of repeated basic operations, i.e., moving one unit of fluid over one unit of distance. As will be described in more detail below, droplets may be formed on a surface of the DMD 20 using surface tension properties of the liquid. Actuation of a droplet is based on the presence of electrostatic forces generated by electrodes placed beneath the surface on which the droplet is located. Different types of electrostatic forces can be used to control the shape and motion of the droplets. One embodiment of a DMD 20 that may be used in connection with the techniques herein creates the foregoing electrostatic forces based on electrowetting principles which relies upon the dependency of the contact angle of the droplet on voltage utilizing a DC or low-frequency AC field. U.S. Pat. No. 6,911,132, (the '132 patent), Pamula et al, Issued Jun. 28, 2005, APPARATUS FOR MANIPULATING DROPLETS BY ELECTRO WETTING-BASED TECHNIQUES, which is incorporated by reference herein, describes examples of different DMD embodiments that may be used in the system 10 of FIG. 1.

In an embodiment of an electrowetting-based DMD as described in the '132 patent, droplets are placed on a surface having control electrodes located beneath the surface. The shape and motion of the droplets may be controlled by switching the voltages of the control electrodes. By sequentially energizing and de-energizing the control electrodes in a controlled manner, one or more droplets can be moved along a path, array, or other formation of control electrodes. As also described in the '132 patent, different operations can be performed on the droplets such as, for example, moving a droplet, merging or mixing two or more droplets into a single droplet, splitting a droplet (such as may be performed after executing a merge operation so as to maintain uniform-sized droplets on the DMD), creating a droplet on a surface of the DMD, and the like.

The DMD 20 may be used for any one or more different applications and operations with a variety of different liquids. For example, the DMD and, more generally, the system of FIG. 1, may be used in connection with sample preprocessing, medical diagnostics, food and environmental monitoring and testing, drug discovery, bioterrorism detection, point of care medical diagnostics, chemical reactions, biological and/or chemical processing using a reagent, serum, biological liquid specimens, and the like. More generally, the DMD may be used with droplets of a sample which are electrolytic, polarizable, or otherwise capable of conducting current or being electrically charged.

As one example, a chemical reaction may be induced using the DMD 20. A droplet containing chemical A can be merged with a droplet containing another chemical B to form a resulting single droplet containing the product chemical C, which is the product of the reaction of A and B. Although analysis, identification and/or detection of the resulting droplet containing product C may be performed "on-chip" on the DMD 20 itself, it may be desirable using the techniques herein to transfer the resulting droplet containing product C "off-chip" to an external analysis instrument or device 22 for further processing in connection with analysis, identification and/or detection. The analysis instrument or device 22 may be, for example, a device that performs mass spectrometry (MS), or liquid chromatography (LC). As further examples, the analysis instrument or device 22 may be a capillary electrophoresis device, photospectrometer or different type of spectrometer, and the like, used for analysis, discovery, and/or identification.

As represented by element 30, droplets from the DMD may be transferred to the analysis instrument or device 22. The technique and/or apparatus used to transfer the droplets from DMD 20 to the instrument 22 may vary in accordance with the particular instrument 22. In following paragraphs and figures, several exemplary embodiments and variations of components of the system 10 are described in which the instrument 22 may be an MS or LC device. However, it will be appreciated by those skilled in the art that the selection of the particular instrument 22 may vary in accordance with the particular application and use of the DMD 20.

Also included in the system 10 is a computer system 24 that may be connected to the DMD 20 and/or instrument 22. The computer system 24 may be used in an embodiment to control the DMD 20 and/or instrument 22.

Figure 2A:
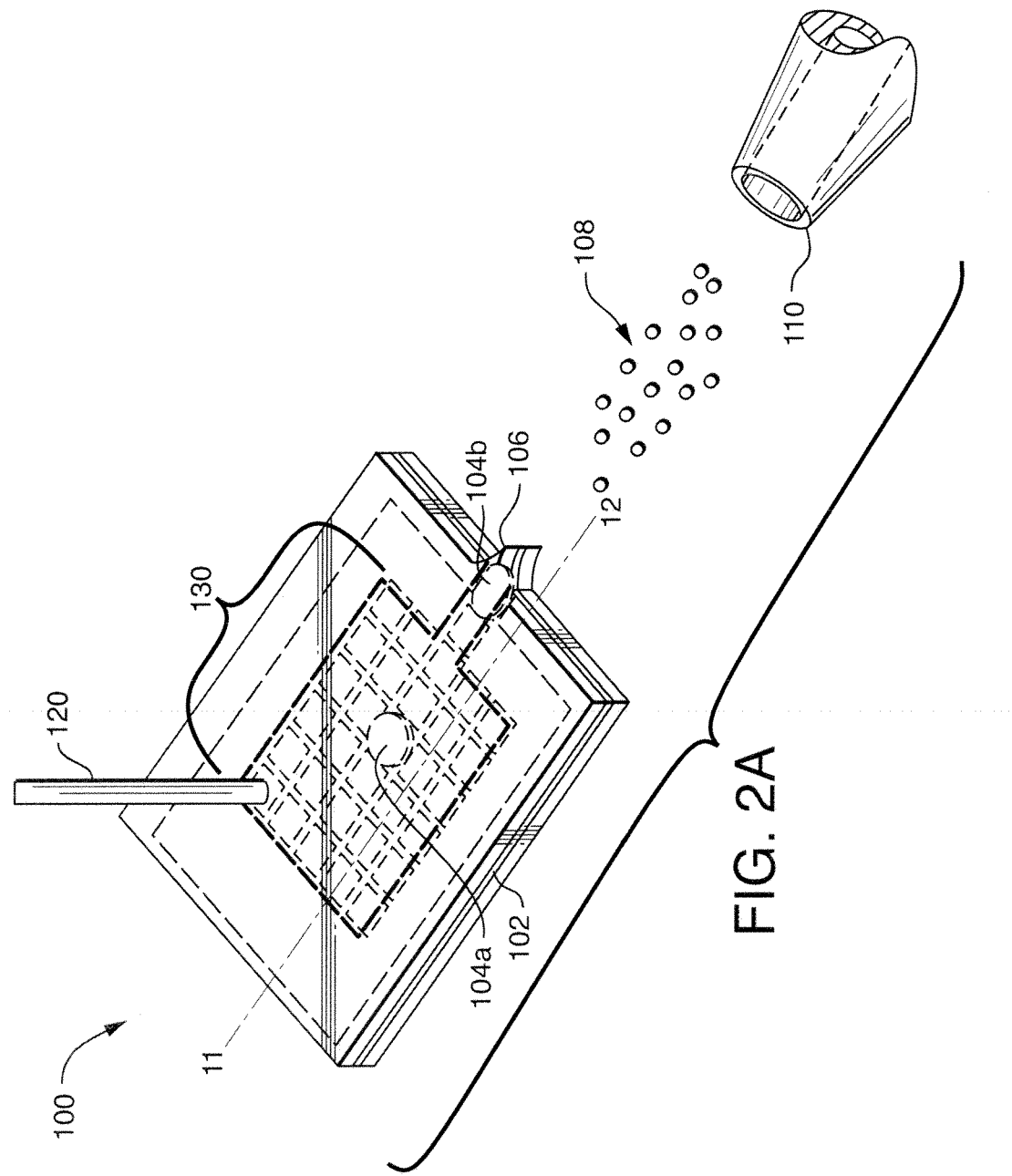
FIG. 2A is an example of an embodiment of the system of FIG. 1 including an analysis instrument that performs mass spectrometry.

Referring to FIG. 2A, shown is an example embodiment of a system that may be used in connection with interfacing the DMD to an MS device. The example 100 includes a DMD 102 having a tip portion 106, droplets 104a and 104b, electrospray 108, sample inlet 120, and an MS inlet 110 of an MS device. The embodiment of the example 100 illustrates a tip portion 106 which is located in the same plane as the DMD 102. An embodiment of the DMD 102 may include a top portion and a bottom portion with a gap or space therebetween. In the example 100, a view of the DMD 102 is shown looking down at the top portion thereof. For purposes of illustration, the top portion and bottom portion are shown as transparent providing a view of the array of control electrodes 130 located beneath a surface of the bottom portion of the DMD 102. The DMD 102 also includes a tip portion 106 extending from the edge of the DMD 102. Additional detail regarding the top and bottom portions and tip comprising embodiments of the DMD 102 are described in more detail in connection with following figures.

Two droplets 104a and 104b are located in the DMD 102 for illustration purposes. One droplet 104a is located inside the DMD 102, between the top and bottom portions thereof, and is on a surface of the bottom portion of the DMD 102 above the planar array of control electrodes 130. The other droplet 104b is located at the tip portion 106 that extends from the edge of the DMD. Upon application of an electrical field between the tip portion 106 and the inlet of the mass spectrometer ("MS inlet 110"), the droplet 104b forms an elongated conical shape, called a "Taylor cone," at the end of the tip. As known in the art, a Taylor cone refers to the cone observed in an electrospray process from which a jet of charged particles emanates. When a small volume of electrically conductive liquid that may be provided from the tip portion is exposed to an electric field, the shape of the liquid starts to deform from the shape imparted by surface tension. As the electrical field becomes more prominent, such as by increasing a voltage at or near the end of the tip portion, a jet of liquid is emitted from the Taylor cone formed at the end of the tip portion and is the start of the electrospray process in which ions may be transferred to a gas phase. Through the generation of the electrospray 108 by this process, the droplets undergo evaporation and breakup into smaller droplets, which lead to the generation of ions that enter the MS inlet 110 for further analysis by the MS device. The use of the foregoing electrospray process to generate ions for mass spectral analysis by the MS device is known in the art as described, for example, in U.S. Pat. No. 4,531,056, Labowsky et al, Issued Jul. 23, 1985, METHOD AND APPARATUS FOR THE MASS SPECTROMETRIC ANALYSIS OF SOLUTIONS, which is incorporated by reference herein, and as also described in The Journal of Chemical Physics (1968), Vol. 49, No. 5, pp. 2240-2249, Dole et al., "Molecular Beams of Macroions", which is incorporated by reference herein.

The distance between the Taylor cone formed at the end of the tip portion and the MS may vary, for example, from 0.1 cm-10 cm. Using the electrospray ionization process described herein, as the liquid stream atomized into droplets, the droplets evaporate creating a plume. As droplets travel from the Taylor cone to MS inlet 110, the droplets evaporate and form positive and/or negative ions which travel to the MS inlet 110 and are analyzed. In one embodiment, the MS inlet 110 may be in the form of a cone as illustrated and a vacuum may be used to draw the particles inward into the MS inlet 110 for analysis. A high electrical field is needed to perform the ionization of the liquid droplets but the voltages used to create the electric field may be varied in accordance with particulars of an embodiment, such as the distance between the Taylor cone and the MS inlet, to achieve the desired ionization process.

An embodiment of the system of FIG. 2A may mount the DMD close to the MS inlet 110 with a distance therebetween that may vary with embodiment. The MS inlet 110 may perform mass spectral analysis and may be implemented using standard components known in the art. For example, an embodiment utilizing the techniques herein may include an MS device having MS inlet 110. As known in the art, commercially available mass spectrometers may include an ion source that produces ions, an analyzer that sorts the ions in some way in accordance with the masses of the ions, and a detector that measures the relative intensities of different masses. A typical ion source may perform electrospray ionization as described herein in generating electrospray 108. An embodiment using the techniques herein may include components for the foregoing analyzer and detector coupled to the DMD 102 so that the DMD 102 is used as described herein as the ion source. An embodiment may arrange the components of the example 100, or portions thereof, in an enclosure. For example, an embodiment may utilize an arrangement so that the electrospray 108 is generated and transferred to the MS inlet 110 in an enclosure.

It should be noted that although the example 100 of FIG. 2A illustrates the tip portion 106 as collinear with the axis of the MS inlet 10, other orientations of the tip portion 106 relative to the MS inlet 110 are possible.

Examples of commercially available mass spectrometers that may be used in an arrangement with the techniques herein include the LCT Premier™ XE mass spectrometry device and the Q-T of Premier™ mass spectrometry device available from Waters Corporation of Milford, Mass.

Droplets may be introduced into the DMD in a variety of different ways. For example, the sample liquid may be introduced to the DMD 102 using the sample inlet 120 via a through hole in the top portion. The sample inlet 120 may be, for example, a pipette, capillary tube, syringe, and the like, used for dispensing the liquid. The sample inlet 120, and other means that may be connected thereto for dispensing the liquid, may provide for dispensing liquid in predetermined amounts as well as a continuous flow of liquid. Introduction of liquid for use with the DMD 102 may be performed using manual and/or automated techniques. It should be noted that liquid may also be introduced into the DMD between the top and bottom portions in accordance with other openings and through-holes that may exist in the top portion. How a droplet may be formed on the array of electrodes 130 is described in more detail in following paragraphs and is also described in the '132 patent. Also, how a droplet may move from a first position in the control electrode array, such as that associated with 104a, to a second position, such as that associated with 104b, is also described in more detail in following paragraphs and also in the '132 patent.

It should be noted that although the tip portion 106 is located on one side of the DMD 102, the tip portion 106 may be located on any side of the DMD 102. Also, an embodiment of the DMD may include more than one tip portion located on any single side and/or on different sides of the DMD 102. Also, although a two-dimensional array arrangement of control electrodes 130 is shown with control electrodes on the bottom layer of a particular shape, variations to the foregoing will be appreciated by those skilled in the art. For example, the control electrodes 130 may be of a different shape and/or size (e.g., circular or other shaped electrodes, all electrodes of the same size and shape, electrode arrangement including electrodes of varying sizes and/or shapes), have a different arrangement (e.g., a single row or column, non-linear formations), and the like, than as illustrated in FIG. 2A.

Figure 2B:
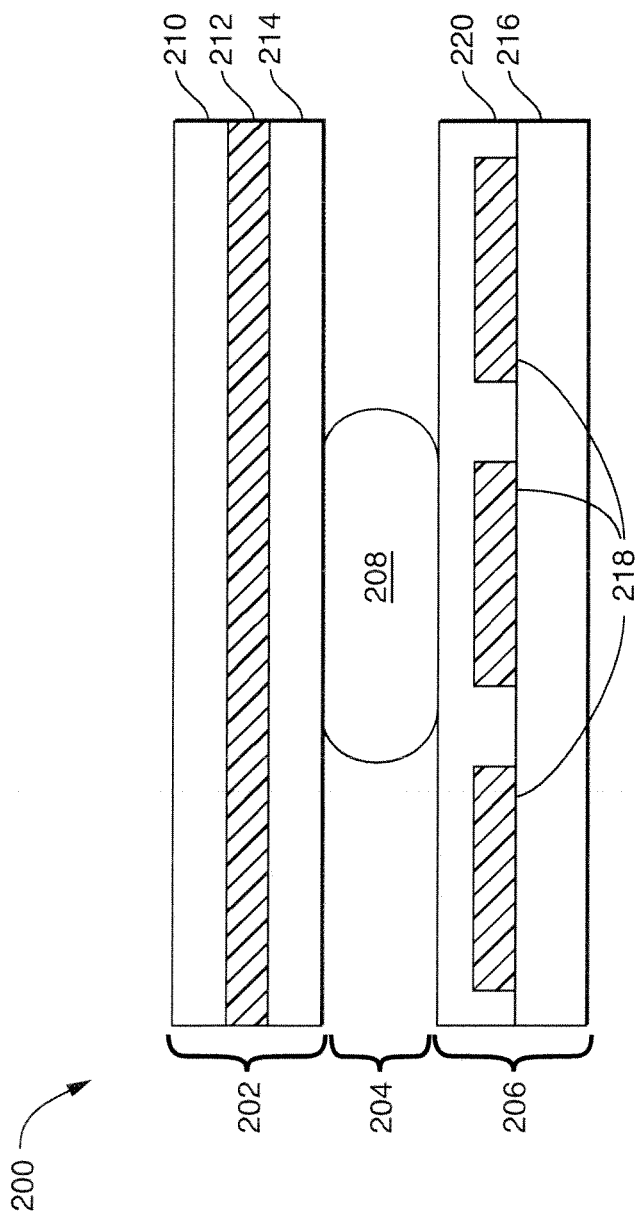
FIG. 2B is an example of a side or lateral view of the digital microfluidic device (DMD) from FIG. 2A taken along the line 11-12 of FIG. 2A.

Referring to FIG. 2B, shown is a side or lateral view of the DMD from FIG. 2A taken along the line I1-I2 of FIG. 2A. The example 200 illustrates the DMD as including a top portion 202, a bottom portion 206, and a gap 204 or space therebetween. The top portion 202 and bottom portion 206 may be arranged with respect to the horizontal plane or other orientation. A droplet 208 may be located on an inner surface of the bottom portion so that the droplet 208 is located between the top and bottom portions of the DMD. The droplet may touch both inner surfaces of the top portion 202 and bottom portion 206 forming the gap 204. The top portion 202 and bottom portion 206 may be parallel, or substantially parallel, to one another. The top portion 202 includes a substrate layer 210 with a continuous ground or reference electrode 212 embedded therein or formed thereon. A thin layer of hydrophobic insulation 214 may also be applied to cover the reference electrode 214. The bottom portion 216 may include a substrate 216 with control electrodes 218 embedded thereon or formed thereon covered by a hydrophobic insulation layer 220. The substrates 210 and 216 may be made out of printed circuit board (PCB) material, glass, or low-temperature cofired ceramic. The control electrodes 218 and the reference electrode 212 may be formed using materials and standard microfabrication techniques. The hydrophobic insulation layers 214 and 220 provide electrical insulation for the electrodes and also create a hydrophobic surface. In one embodiment, the hydrophobic insulation layer 220 may be formed over and around the control electrodes 218 using a layer of PARYLENE C followed by a coating of TEFLON. The layer 214 may be formed using a coating of TEFLON. The TEFLON coatings of 214 and 220 are included on the inner surfaces of the top and bottom portions facing the gap 204. As a variation to the foregoing, an embodiment may coat the reference electrode 212 with a coating of PARYLENE C prior to the TEFLON coating to provide electrical insulation in an embodiment. The gap 204 may be in the range, for example, of 0.01-1.0 mm. Examples of materials that may be used in connection with providing electrical insulation in an embodiment may include silicon oxide, silicon nitride, TEFLON, and the like. Examples of materials that may be used in connection with forming a coating or layer providing hydrophobicity include fluorocarbons, TEFLON, and the like. Generally, an embodiment may form coatings as described herein over the reference electrode 212 and over and/or around the control electrodes 218 so that materials providing insulation and hydrophobicity are as thin as possible. The thicker the foregoing, the larger the voltage needed to achieve the electrowetting effect. Additional details regarding specific materials, thicknesses, possible size of the gap between top and bottom portions, spacing between control electrodes, and the like, that may be used in an embodiment are described, for example, in the '132 patent. U.S. Patent Publication No. US2006/0194331, Published Aug. 31, 2006, Pamula et al., U.S. patent application Ser. No. 11/343,284, Filed Jan. 30, 2006, APPARATUSES AND METHODS FOR MANIPULATING DROPLETS ON A PRINTED CIRCUIT BOARD, which is incorporated by reference herein, describes how to make a DMD using PCB material. An embodiment may use different materials and techniques known in the art in connection with manufacturing of the DMD. Examples of the materials, techniques for manufacturing and/or producing the DMD, and other details that may be used in an embodiment are described herein, in the '132 patent, U.S. Patent Publication No. US2006/0194331, and U.S. Pat. No. 7,147,763, Dec. 12, 2006, Elrod et al., APPARATUS AND METHOD FOR USING ELECTROSTATIC FORCE TO CAUSE FLUID MOVEMENT, all of which are incorporated by reference herein. It should be noted that the foregoing are some examples of materials, techniques, and the like, that may be used in an embodiment. Additional embodiments, including variations to the foregoing, will be appreciated by those skilled in the art.

In the array or other arrangement of control electrodes 218, each such control electrode may be addressed independently so that a voltage may be independently applied to, and removed from, each control electrode. With reference back to FIG. 1, an embodiment may include the computer system 24 which is programmed using instructions to activate and deactivate selected ones of the control electrodes of the DMD (e.g., by increasing and decreasing voltages) according to a predetermined sequence causing droplets to be actuated to particular electrodes to perform desired operations, such as mixing or merging of droplets. In one embodiment, each control electrode may have a voltage applied thereto in a range from ground to 120V DC although other ranges may be used as well as an AC power supply. The reference electrode 212 may be grounded or set to a reference potential. By activating a control electrode by increasing the voltage thereto to a threshold value, the region of the bottom portion covering the control electrode becomes hydrophilic so that a droplet on a deactivated neighboring or adjacent control electrode moves to the region associated with the activated control electrode. For example, with reference to FIG. 2B, the control electrodes 218 may be initially "off" or in a state of deactivation so that the control electrodes may initially be at ground or floated (e.g. no voltage applied). In order to move the droplet 208 to the right, the control electrode to the right of the droplet 208 may be activated or turned "on" by increasing the voltage thereto. The voltage may be increased to a threshold value and, as the voltage is increased, the rate at which the droplet moves may also increase. The threshold voltage and rate at which a droplet may move as the voltage is further increased in a control electrode may vary with the composition of the droplet.

Figure 2C:
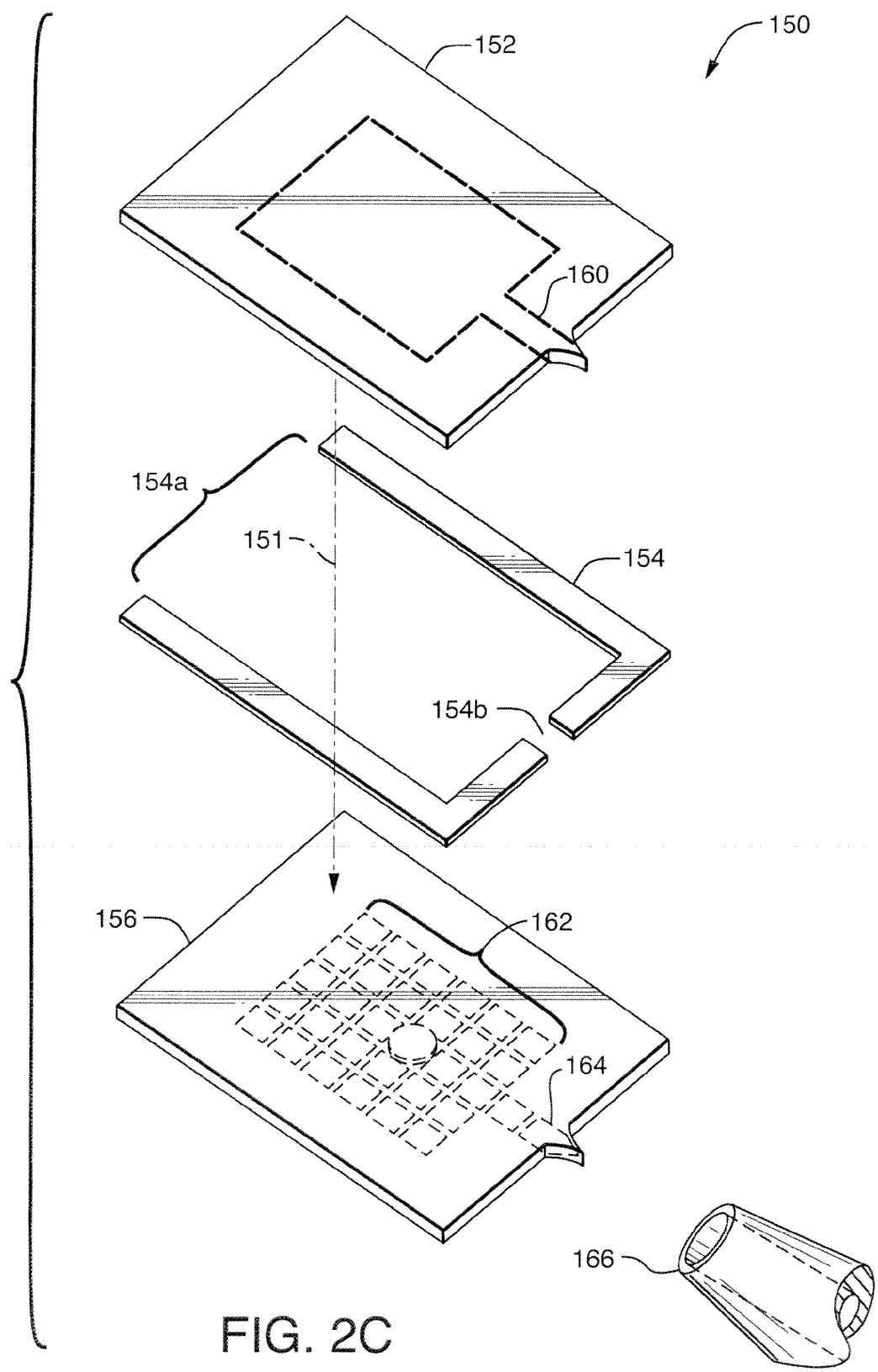
FIG. 2C is an example of a more detailed view of an embodiment of a DMD.

Referring to FIG. 2C, shown is an example illustrating an exploded view of the DMD from FIG. 2A. The example 150 illustrates a DMD as including a top portion 152, a spacer 154 and a bottom portion 156. The elements 152, 154 and 156 may be combined and arranged on top of one another as illustrated by the arrow 151 to form the DMD 102 as illustrated, for example, in FIG. 2B. The top portion 152 and bottom portion 156 may be as described above. The spacer 154 may be used to create the gap or space between the top and bottom portions in which the droplets are located. The spacer 154 may be made of a polymeric material. It should be noted that in connection with FIG. 2C, as well as others such as FIG. 2A, the spacer 154 provides a gap layer between the portions 152 and 154. Although the figures illustrate the gap layer being enclosed except for an opening on one side 154a of the DMD and an opening 154 at the tip portion, it should be noted that all sides of the gap layer (including 154a) may be enclosed with the openings as described herein at the tip portion and one or more inlet ports which may be located on a surface or side of the DMD (e.g., inlet port may be located in a side that is either perpendicular to the DMD and/or in the plane of the DMD).

The size of the droplets that may be used in an embodiment vary in accordance with the size of the gap layer created by the spacer 154. The arrangement of 152, 154 and 156 may be held in place by a clamp or other means for coupling and securing the foregoing as illustrated in FIG. 2C. In the example 150, the reference electrode 160 is illustrated as having a voltage U0. Each control electrode of 162 is denoted as having a voltage of U1($i$), i=1 to N, inclusively, in which there are N control electrodes and represents a particular one of the N control electrodes. The control electrode located on the tip portion, also referred to as the "tip electrode" 164, is denoted as the "N+1" control electrode having a voltage U1(N+1). The MS inlet 166 has a voltage associated therewith denoted as U2.

In one embodiment, examples of typical voltages that may be applied are: U2=ground, U0=+/−3 kV, U1=U0+100 V. Other typical voltages that may be applied are, for example, U2=+/−3 kV, U0=GND, U1=100 V. U1 represents the voltage that may be applied to the control electrodes to achieve an "on" or activation state. The foregoing are illustrative of voltages that may be used in an embodiment although it will be appreciated by those skilled in the art that other voltages may also be used to create the voltage differences sufficient to achieve the electrowetting effect and electrospray. For example, a voltage difference of 10-200V between reference electrode 160 and control electrode 162 may be typically sufficient to achieve the electrowetting effect and a voltage difference of 1000-5000V between reference electrode 160 and MS voltage 166 may be typically sufficient to create the electrospray. When a voltage is applied at control electrode i, the surface above the control electrode becomes hydrophilic based on the phenomenon as described herein and known in the art as electrowetting. When the control electrodes are activated, by applying a sufficient level of voltage thereto, in the proper sequence, the change of contact angle can be used to move droplets and achieve other operations, such as merging two droplets or splitting one droplet into two droplets, and other operations as described herein.

Figure 2D:
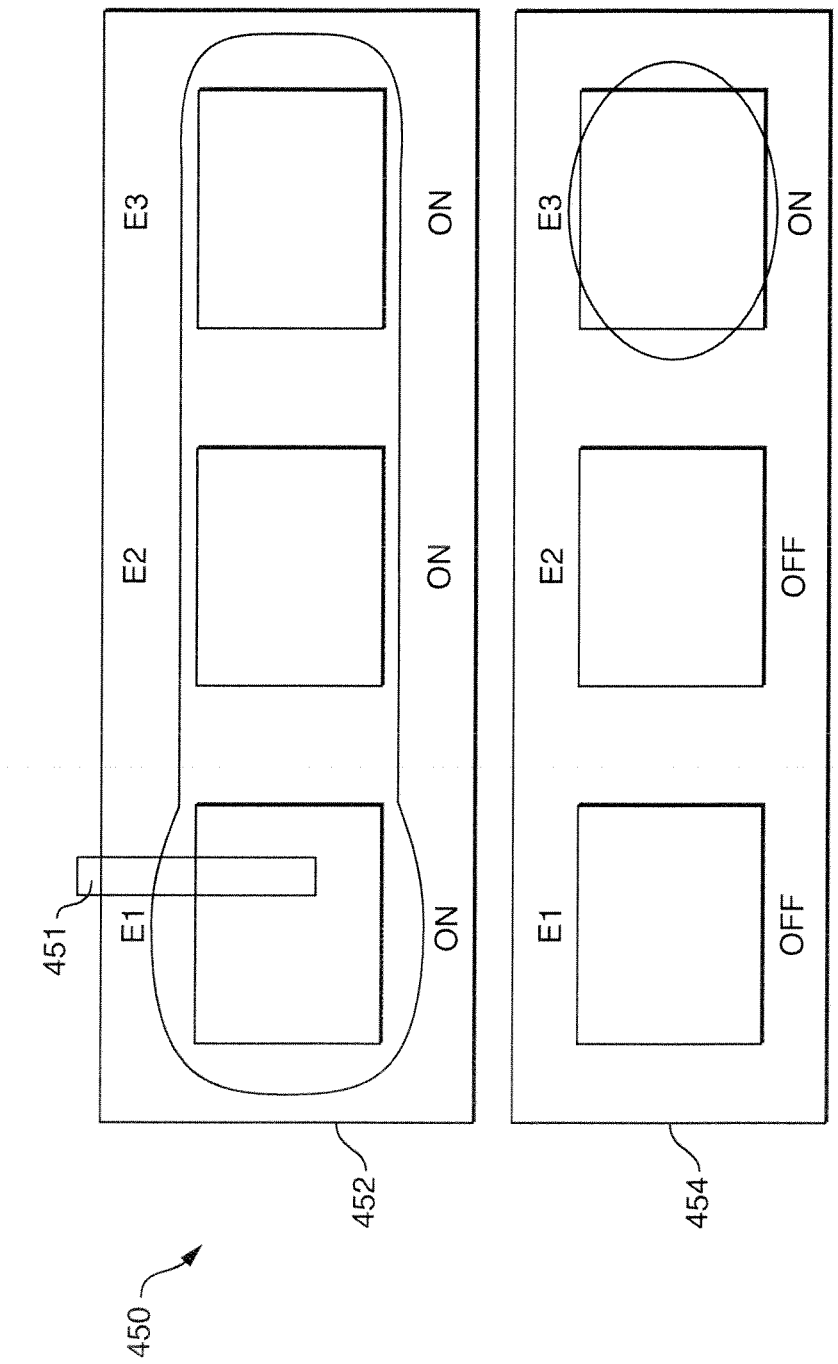
FIGS. 2D and 2E illustrate use of electrowetting principles for performing operations using the DMD.

Referring to FIG. 2D, shown is an example illustrating how voltages may be applied to form a droplet. In the example 450, included are control electrodes E1, E2 and E3. Element 452 illustrates a first or starting state for each of the electrodes E1-E3. For purposes of illustration, the liquid may be dispensed in a predetermined amount from an inlet channel 451 over electrode E1. Control electrodes E1-E3 may be activated by applying a voltage to each to draw in fluid from 451. As an example, a voltage of 100V may be applied to each of E1-E3 causing the liquid to be drawn in and dispersed over the surface thereof as illustrated in 452. For purposes of illustration, the "on" or active state of a control electrode may correspond to applying a voltage of 100V thereto. The "off" state may correspond to not applying any voltage to a control electrode, or otherwise held at a reference or ground voltage. E2 may then be deenergized or placed in the off state causing the liquid dispersed over E1-E3 to split. The portion of the liquid over E1 retracts back into the inlet channel 451 and the portion formed over E3 as illustrated by 454 is the newly formed droplet. In connection with element 454, E3 may remain active or on by keeping the 100V applied thereto. The voltages as applied to E1 and E2 may be removed or made to float causing E1 and E2 to transition to the off or deactivated state. As illustrated in 454, the result is that the droplet is formed on E3 and may be manipulated further, for example, as will now be described in connection with FIG. 2E.

Figure 2E:
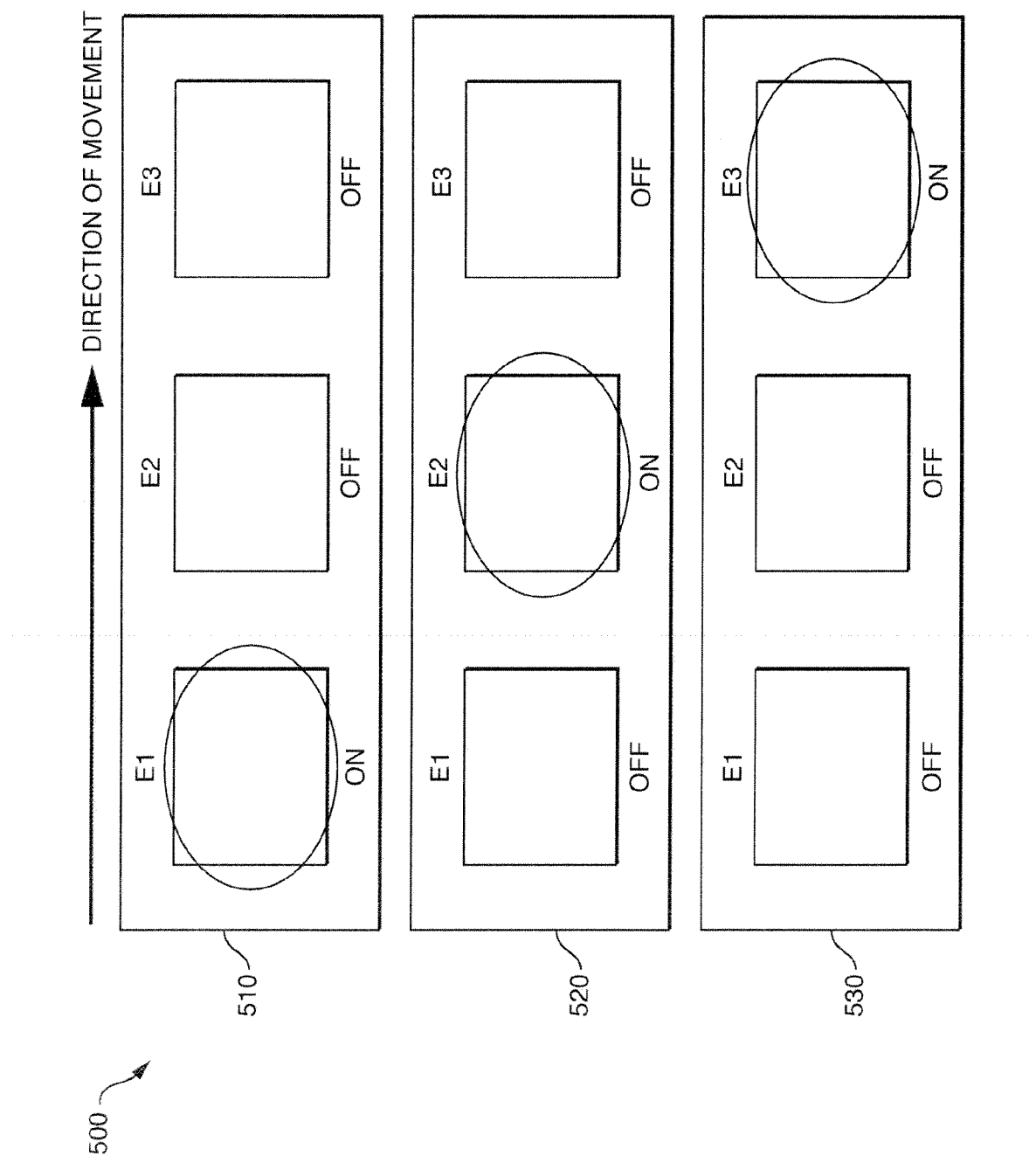

Referring to FIG. 2E, shown is an example illustrating how voltages may be applied to cause a droplet to move across a series of linearly arranged control electrodes. The example 500 illustrates a basic move operation although other operations are possible by similarly activating and deactivating selected control electrodes. The example 500 includes 3 electrodes E1-E3 as also illustrated in FIG. 2D. The element 510 represents a first or initial state of each of the control electrodes E1-E3. In this first state, E1 may be energized and E2 and E3 may be at ground or floating. The droplet is initially over E1. In a second step as illustrated by 520, control electrode E2 has a voltage applied thereto so that E2 is in the on state while E1 and E3 remain in the off state. Application of voltages and states of control electrodes of 520 results in the droplet moving from the surface covering E1 to that of E2. In a third step, as illustrated by 530, control electrode E3 has a voltage applied thereto so that E3 is in the on state while E1 and E2 remain in the off state. Application of voltages and states of control electrodes of 530 results in the droplet moving from the surface covering E2 to that of E3.

In connection with the foregoing as illustrated in FIGS. 2D and 2E, a computer system (such as the computer system represented by element 24 of FIG. 1) may be programmed using instructions to activate and deactivate selected control electrodes of the DMD according to a predetermined sequence causing droplets to be actuated to particular electrodes to perform desired operations, such as moving, mixing or merging of droplets, and other operations. Appropriate electrical connections, switches, power supplies or sources, and the like, as known in the art may be used in providing the voltages to the control electrodes and reference electrode and for allowing the selection of such voltages to be controlled by a computer system or other programmed control device to perform processing as described herein.

Based on the electrowetting phenomena and proper sequencing of voltages, an experiment or other processing may be performed on the DMD resulting in the formation of a droplet. The resulting droplet may be moved into the tip portion of the DMD on the surface over the control electrode N+1 located in the tip portion. (The control electrode N+1 located in the tip portion may also be referred to herein as the "tip electrode"). This movement may be performed by appropriately activating and deactivating selected control electrodes until the droplet is located in the surface area of the bottom portion above the tip electrode by activating or turning on the tip electrode and deactivating or turning off neighboring control electrodes (e.g., those control electrodes adjacent to the tip electrode so that the droplet is drawn to the tip over the tip electrode). For example, the droplet may be drawn in a linear motion as described in connection with FIG. 2E by controlling the voltages in sequence as described. The tip electrode may be, for example, electrode E3. Once the droplet reaches the tip electrode, the tip electrode may remain in the activate or on state, or otherwise made to float. Subsequently, a voltage U2 may be applied to the MS inlet to create the Taylor cone and initiate the electrospray and analysis of the chemical species contained in the droplet.

Figure 3A:
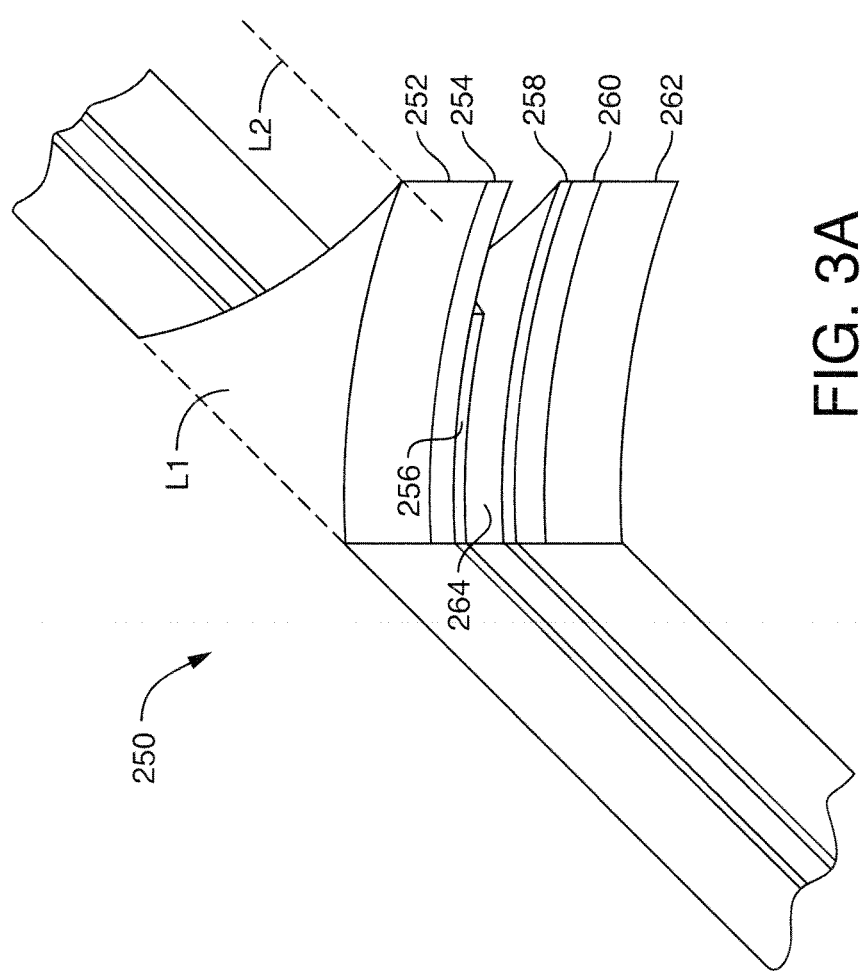
FIGS. 3A-3C are examples of embodiments of a tip portion of the DMD.

Referring to FIG. 3A, shown is an example illustrating a first embodiment of the tip portion of the DMD in more detail. For purposes of simplicity of illustration, the droplet located at the tip portion is not shown in this example. The elements 252, 254, 256, 258, 260 and 262 may be as described elsewhere herein. The opening 264 corresponds to the opening in the gap layer at the tip portion. As illustrated, the tip portion is formed with 2 sides extending from the DMD toward the end of the tip portion forming a triangular-shaped tip portion and having the 2 sides thereof completely open or otherwise not enclosed. The tip electrode 260 may be extended to the edge or end of the tip portion. The tip may come to a sharp point. With respect to the tip portion, both the reference electrode and the tip electrode located thereon may be covered with insulation layers, with the exception of a small section of the reference electrode which makes electrical contact with the droplet when in the tip portion. In one embodiment, the tip portion may be 0.5 to 5 mm in length as measured from L1 to L2 (e.g., the end of the tip point).

It should be noted that in connection with the tip portion as described herein, an embodiment may utilize a tip portion which has a pointed end as illustrated. However, the techniques herein may also be used with a tip portion having a more rounded or blunted end although variations in the voltages may be needed in order to achieve the Taylor cone and electrospray process.

In connection with the arrangement of FIG. 3A, a voltage may be applied to the reference electrode 254 making electrical contact with the droplet in the tip portion. The voltage may be applied in connection with the techniques herein to generate an electrical field between the droplet and the MS inlet sufficient to create a Taylor cone at the end of the tip portion and an electrospray. As a first variation to what is described and illustrated in connection with FIG. 3A, the reference electrode 254 may be completely covered by the top insulation layer 256. In this first variation, the layer 256 may be hydrophobic and electrically conducting so that a voltage may be applied to the reference electrode 254 or layer 256 in generating the foregoing electric field. As a second variation, the electrode 254 may be completely covered by layer 256 and layer 256 may be hydrophobic and electrically insulating. In this second variation, an external metal layer or other conductive material may be deposited on the tip portion in order to create an electrode and make electrical contact with the droplet. The external metal or conductive layer may be applied using a variety of techniques known in the art such as, for example, by sputtering or evaporation.

Figure 3B:
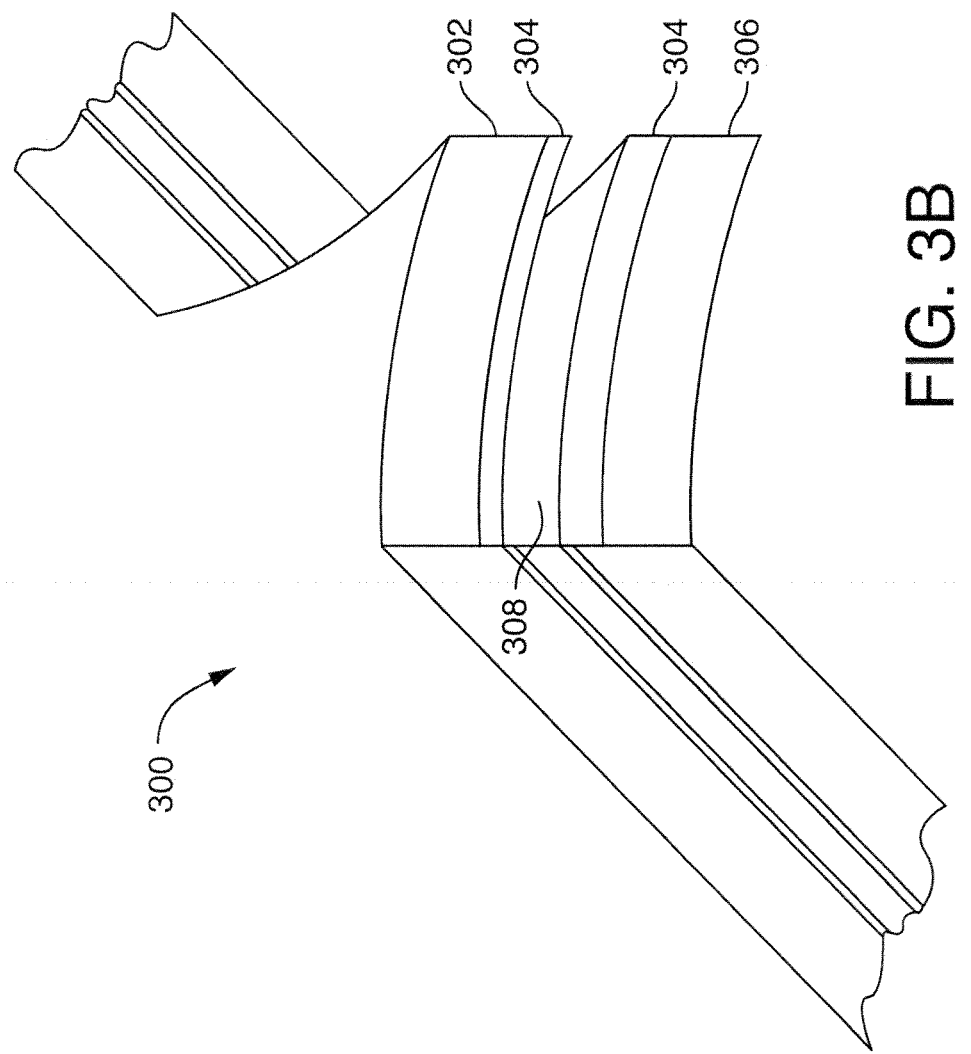

Referring to FIG. 3B, shown is an example illustrating a second embodiment of the tip portion of the DMD in more detail. The elements 302 and 306 are as described elsewhere herein. In this embodiment, no tip electrode is included in the tip portion of the DMD. Thus, with reference back to FIGS. 2A and 2C, control electrode N+1 may be omitted. Rather, in the example 300 at the tip portion, the top substrate 302 of the top portion is covered with a hydrophilic surface coating or layer 304. Similarly, the bottom substrate 306 of the bottom portion is covered with a hydrophilic surface coating or layer 304. The hydrophilic surface coating or layers 304 of the tip portion may be formed, for example, by coating the inner surfaces of the top and bottom portions located in the tip portion with cellulose polymer, polyacrylamide, silicon dioxide, or titanium, aluminum, or by chemically modifying the inner surfaces where 304 is located by gas plasma treatment, plasma polymerization, or laser treatment. In the case where the inner surfaces are coated, the thickness of the coating layer 304 may be, for example, in range of 10 nm to 100 μm, inclusively. With the exception of the variation for the tip portion as illustrated in the example 300, it should be noted that the top portion and bottom portion of the DMD may be as described and illustrated in previous paragraphs, such as those in connection with FIG. 2B.

Using the foregoing arrangement of FIG. 3B for the tip portion, the surfaces in contact with the droplet at the tip portion are locally hydrophilic in order to draw the droplet to the tip portion from an area over a control electrode adjacent to the tip electrode. The insulation layers covering the bottom and top substrates elsewhere in the DMD are still hydrophobic as described herein.

Figure 3C:
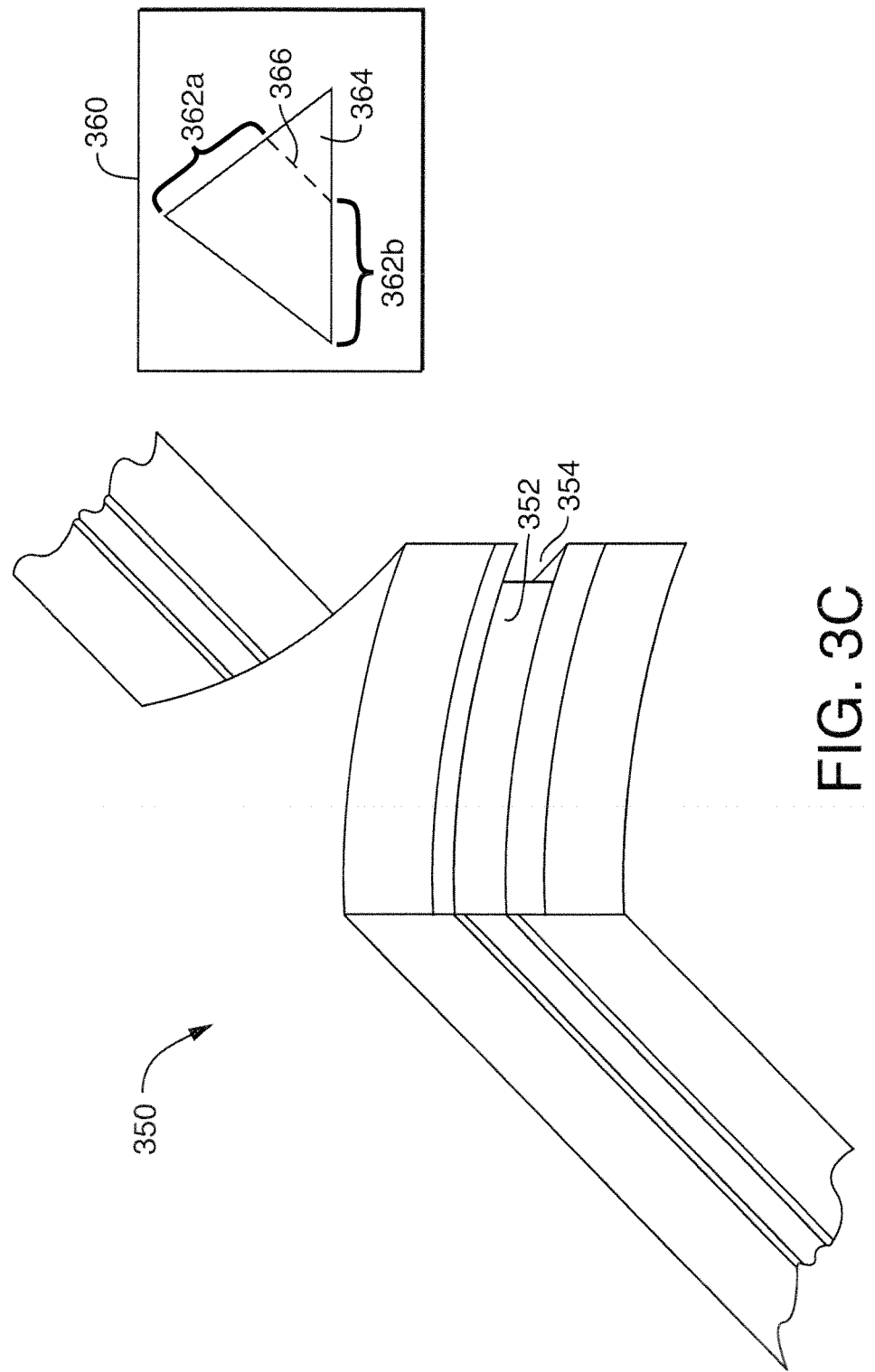

In the embodiments of the tip portion as illustrated in FIGS. 3A and 3B, the tip portion has open sidewalls. In other words, there is no enclosure of any part of the sides of the tip portion in the gap layer formed between the top and bottom portions as illustrated, for example, in the opening 264 of FIG. 3A and opening 308 of FIG. 3B. As a variation to the foregoing, an embodiment is illustrated in FIG. 3C with sidewall enclosures of the tip portion leaving an opening 354 at the end of the tip portion. The example 350 illustrates a tip portion having a sidewall enclosure 352. Although not shown due to the view illustrated in 350, the other face of the tip portion may also similarly have a sidewall enclosure leaving only a small tip opening 354 at the end of the tip portion so that fluid can exit therefrom. An embodiment using sidewalls may have a tip portion formed in accordance with a tip electrode as described in connection with FIG. 3A or may have a tip portion formed in accordance with a tip portion as described in connection with FIG. 3B.

Element 360 may represent the tip portion of the DMD having enclosing sidewalls extending as illustrated along each of 362a and 362b to the line 366. Element 364 may represent the tip opening. In one embodiment, the tip opening 354 in the tip portion may extend from line 366 to the end of the tip portion. The line 366 may represent the width of the tip opening which, in one embodiment, may be 10-100 microns.

With reference to an embodiment using the arrangement of FIG. 3B having open sidewalls as illustrated, or an embodiment of FIG. 3B having enclosed sidewalls as illustrated in FIG. 3C, different techniques may be used in connection with applying a voltage thereto to generate an electric field as described herein to create the Taylor cone and electrospray. An embodiment may utilize the arrangements as illustrated in FIG. 3B with open or closed sidewalls with a first variation. In this first variation an additional electrode is created at the tip portion, for example, by deposition of an external conductive layer, such as a metallic layer, as described above in connection with FIG. 3A variations.

As a second variation from that illustrated in FIG. 3B having open or closed sidewalls, the reference electrode in the top portion may be extended into the tip portion with a small portion thereof exposed to make electrical contact with the droplet when a voltage is applied to the reference electrode. In this second variation, there is no control electrode in the tip portion so that the bottom portion may be as illustrated in FIG. 3B in combination with the top portion as illustrated in FIG. 3A. As a third variation, the top and bottom portions may be as in the foregoing second variation but the top insulation layer 256 may be both hydrophilic and electrically conducting. As an example, layer 256 in the top portion may be hydrophilic conducting carbon black.

As described above with reference to FIG. 2A, the embodiment of the example 100 illustrates a tip portion 106 from which the electrospray 108 may emanate with the appropriate voltage settings to the tip portion 106 and MS inlet 110 creating a sufficient electrical field. The embodiment of 100 has the tip portion 106 located in the same plane as the DMD 102, or substantially so positioned.

An additional embodiment is described in following paragraphs with reference to FIG. 4 in which the DMD 102 does not include a tip portion 106. Rather, an arrangement is described in which the DMD 102 is alternative coupled to a tube having a tip from which an electrospray is generated. The tube is located out of plane with respect to the DMD 102.

Referring to FIG. 4, shown is an example of another embodiment of a DMD that may be used with the techniques herein with an MS device. As described above, the example 400 provides a means by which the DMD is interfaced to the MS device using an out-of-plane tube. The example 400 includes a DMD 420 as described elsewhere herein with a few variations. One variation is that control electrode N+1 or the tip electrode, may be omitted since there is no tip portion of the DMD. The example 400 also includes a tube 406 having an end tip that is inwardly tapered and located in a substantially perpendicular arrangement with respect to the plane of the DMD 420. The droplet 402 may be moved using the techniques herein to place the droplet on top of the surface of the control electrode N 404. There may be a hole formed through the bottom portion of the DMD into which the tube 406 is inserted. The droplet exits the DMD through the hole in the bottom portion and into the tube 406 as illustrated which is perpendicular to the plane of the electrode array. A first end of the tube may be connected to the DMD 420 with a second opposing end of the tube 406 being inwardly tapered forming a small opening therein at the tip of the second end through which droplets exit. The tube 406 may be made, for example, of metal or another conductive material to provide sufficient electrical contact between electrode N and the droplet when the droplet is at the tip of the second end of the tube 406 from which the droplets exit. As another example, the tube 406 may be made of a polymeric material or may consist of a pulled fused silica capillary. At least the tapered portion located at the second end of the tube 406 may be externally coated with an electrically conductive coating, such as a metallic coating, also providing electrical contact between the control electrode N and the droplet when at the tip of the second end of the tube 406. For any of the foregoing examples, the inside surface of the tube 406 may also be hydrophilic. When a droplet is moved to electrode N 404 using electrowetting techniques as described herein, capillary action draws the droplet into the tube at the first end coupled to the DMD and toward the tip located at the second opposing end of the tube. Subsequently, application of an electric field between control electrode N and the MS inlet 410 creates a Taylor cone at the tip (e.g. located at the second end) of the tube and an electrospray 408, as described herein in connection with other embodiments. In one embodiment, the tube may be 1 to 7 cm in length with an inner diameter from 25 to 250 µm that tapers to 5-50 µm at the end having the opening facing the MS inlet 410.

In connection with providing an electric field for creating the Taylor cone and electrospray with reference to FIG. 4 when a sufficient voltage is applied to the control electrode N, the droplet may make electrical contact with an exposed portion of the electrode N. As a variation to the embodiment 400 of FIG. 4, the tube 406 may have one or more electrodes located therein so that the electric field causing the Taylor cone and electrospray may be formed using the one or more electrodes in the tube 406 rather than the control electrode N 404. In such a case, the droplet in the tube 406 makes electrical contact with the electrode in the tube 406 to which the voltage is applied. Such electrical contact may be made, for example, by having a tube 406 formed from a conductive material, exposing a portion of the one or more electrodes in the tube 406 so as to have contact with the droplet when in position at the second end of the tube, or other means for providing electrical contact necessary between the droplet and the energized electrode to which the voltage is applied.

Besides the foregoing, an electric field between the MS inlet 410 and droplet may be achieved in other ways some of which will now be described. As a first example, the tube 406 may be metallic or formed using another electrically conductive material so that the electrical potential can be applied directly to the tube rather than the control electrode N. As a second example, although the tube may consist of non-conductive materials, the tube, or at least the tip of the tube formed by the tapered end facing the MS inlet, may be coated externally with an electrically conductive material and have the electrical potential applied thereto. For example, if the tube is formed using pulled fused silica, the tube may be coated with a sufficient layer of gold or other metallic coating to which sufficient voltage is applied.

It should be noted that although the tube is shown as extending from one particular location in the bottom portion, an embodiment may have a tube similarly inserted in a hole at another location in the bottom portion selected with respect to another control electrode. Additionally, although only a single hole in the bottom portion and tube inserted therein is illustrated in the example 400, an embodiment may also have an arrangement with multiple holes and associated tubes providing for a plurality of places at which a droplet may exit the DMD for transferring to an MS inlet for further analysis.

Described above are variations of the DMD and associated means and techniques by which the DMD may be used to interface with, and transfer a droplet to, an MS device for further analysis. With reference back to FIG. 1, what will now be described are examples of embodiments in which the analysis instrument or device 22 is an LC device.

Figure 5:
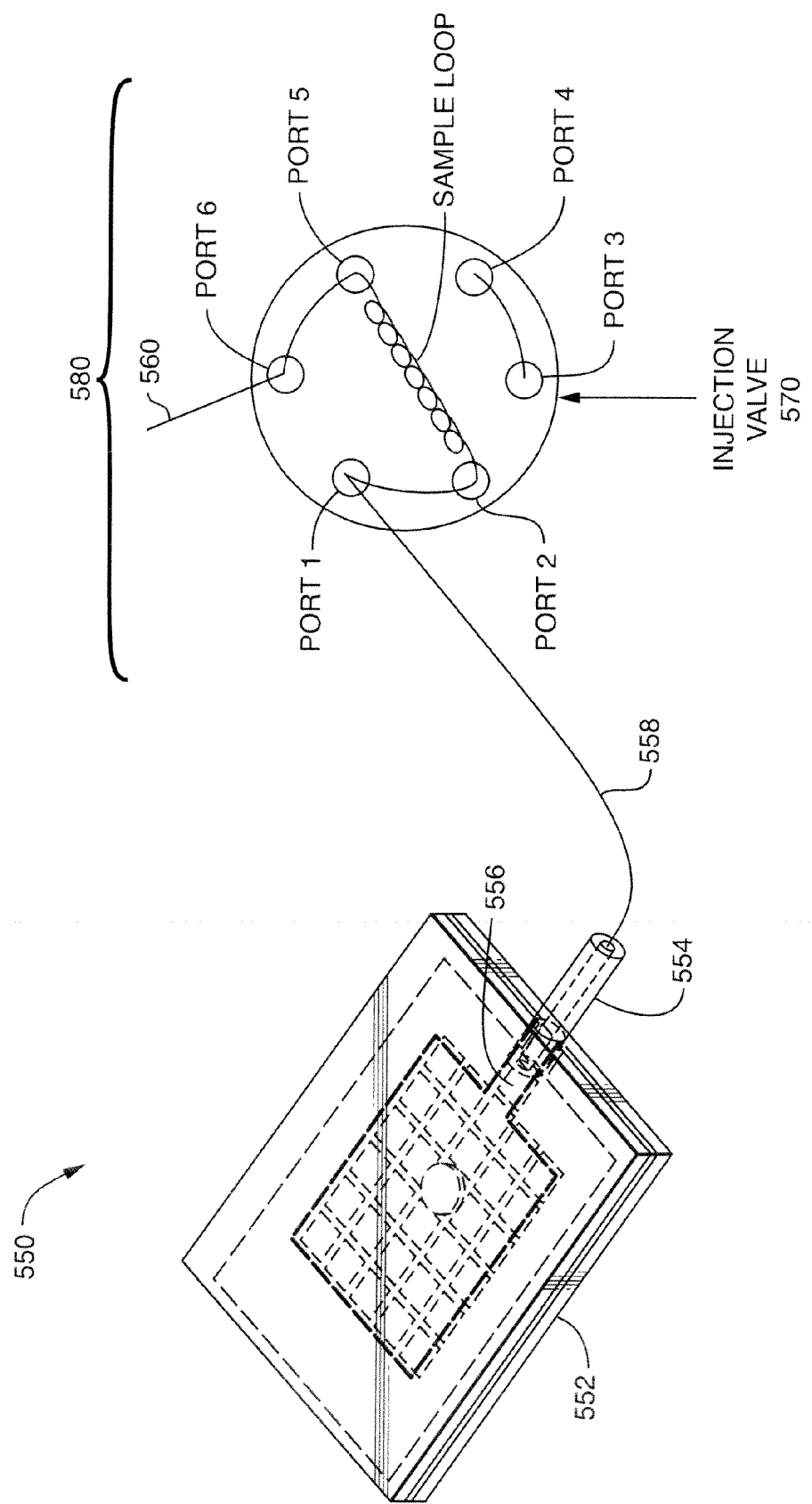
FIGS. 5-6 are examples illustrating a first embodiment of the system of FIG. 1 including an analysis instrument that performs liquid chromatography, capillary electrophoresis or another type of analysis on the liquid contained in the droplet.
Figure 6:
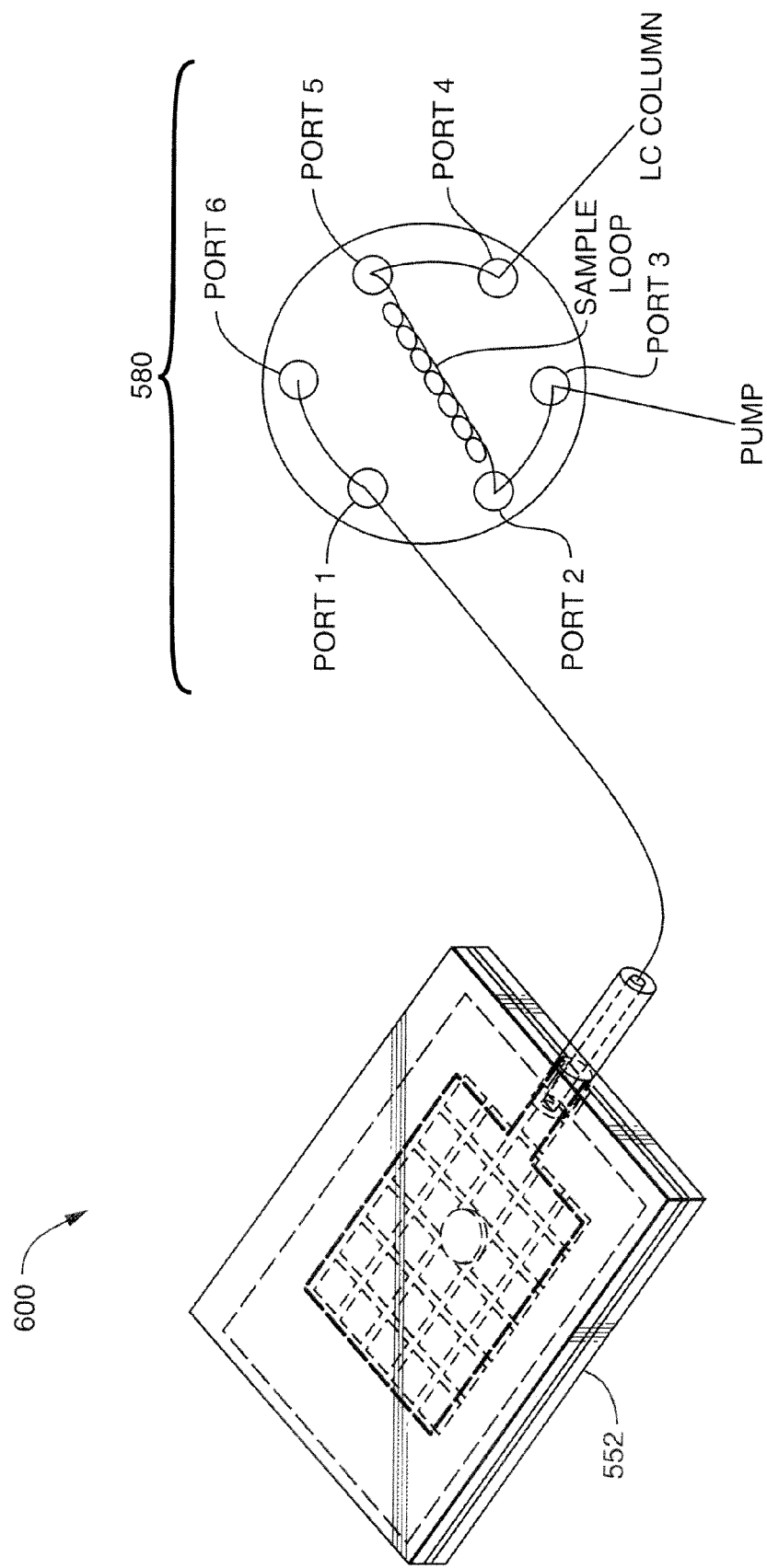

Referring to FIG. 5, shown is an example embodiment of a system that may be used in connection with interfacing the DMD to an LC device. The example 550 includes a DMD 552, a fitting 554, and a tube 558. Also illustrated are portions of components, such as the pump 560 and injection valve 570, that may be included in the LC device 580. The DMD 552 may be as described elsewhere herein using an embodiment having N control electrodes. The fitting 554 may be fitted and coupled to the DMD through an opening in one of the sides DMD so that a droplet located on the bottom portion above electrode N may be transferred into the fitting 554 and tube 558 providing the droplet to the LC device. In the example 550, a fluidic connection from the DMD to the LC device is formed using the fitting 554 and tube 558. The tube 558 connects to the fitting 554 at a first end and, the other end of the tube 558 is attached to port 1 of a 6-port valve of an LC device. When a droplet is moved to a location on a surface of the bottom portion over control electrode N, negative pressure may be applied at the pump attached to port 6, resulting in the droplet being aspired into the tube 558 and flowing into the sample loop of the injection valve 570. Subsequently, as illustrated in FIG. 6, the valve is switched (such as rotated in a clockwise manner) so that the sample loop is in the fluid path of the LC column. A pump connected to port 3 may then be used to push the liquid out of port 4 and into the column of the LC device for analysis.

The tube 558 and fitting 554 may be made of a polymer material, metal or fused silica. The inside of the tube and fitting may be hydrophilic but may also have inner surfaces which are not since the droplets are aspirated by the pump described herein. The inner diameter of tube may be, for example, 25 to 360 μm. The tube may have a length sufficient to facilitate physical connection between the DMD and the LC device 580.

The embodiment illustrated in FIGS. 5 and 6 utilize an in-plane fitting 554 and tube 558 to provide a means by which droplets may be transferred from the DMD to an LC device for analysis. It should be noted that although the arrangement of FIGS. 5 and 6 illustrate an embodiment in which the analysis instrument performs LC, the arrangement of FIGS. 5 and 6 may include an analysis instrument that alternatively performs capillary electrophoresis or another type of analysis on the liquid contained in the droplets transferred from the DMD.

Figure 7:
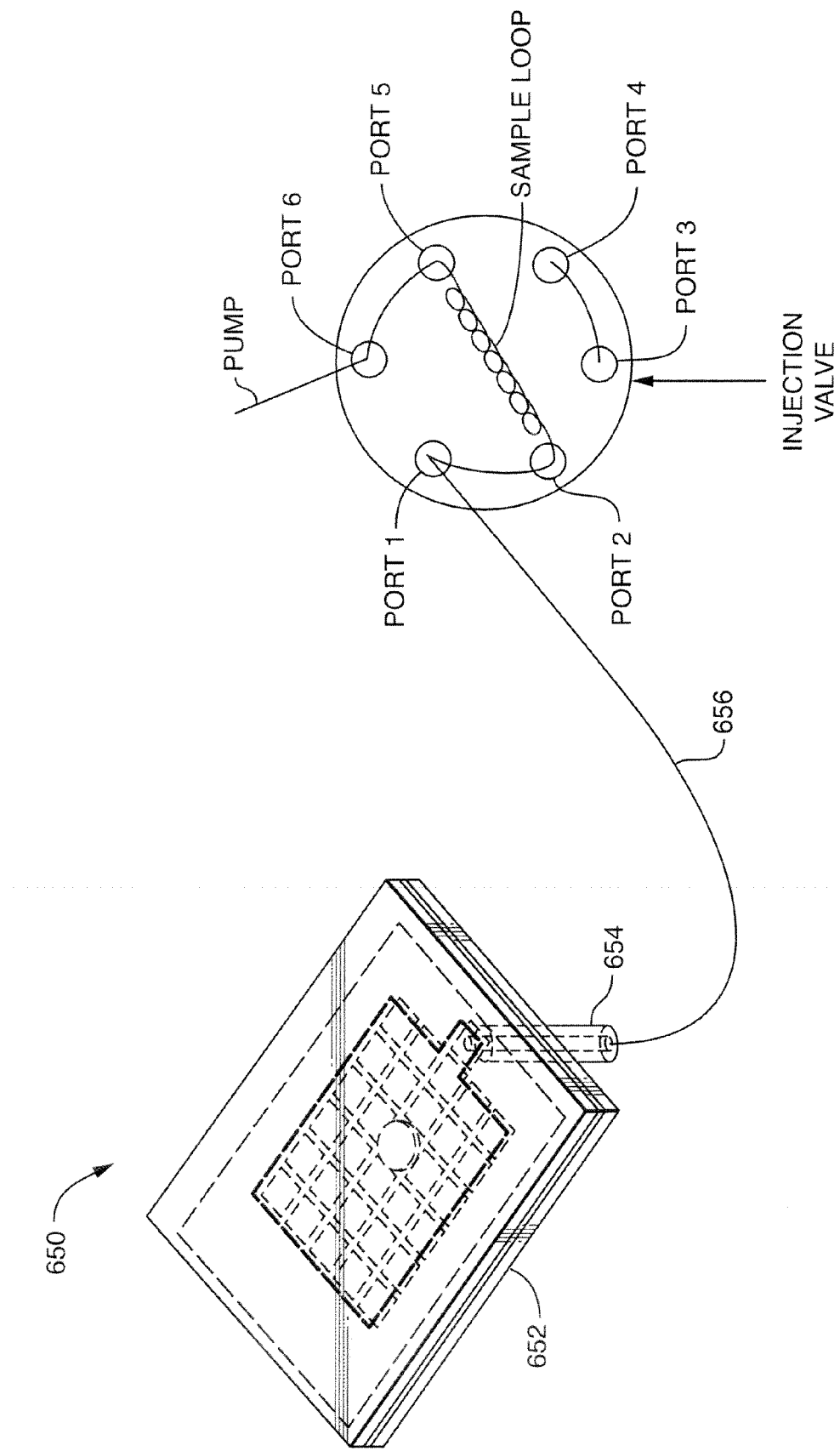
FIG. 7 is an example illustrating a second embodiment of the system of FIG. 1 including an analysis instrument that performs liquid chromatography.

Referring to FIG. 7, shown is an example of another embodiment of a system that may be used in connection with interfacing the DMD to an LC device. The example 650 includes components similar to those as described in FIG. 6 with some variations. In the example 650, the fitting 654 is located out of plane with respect to the plane of the DMD 652. In the example 650, there is an exit port or hole located in the bottom portion of the DMD into which the fitting 654 is inserted. In the example 650, the fitting 650 is perpendicular, or substantially perpendicular, to the plane of the DMD. As described herein in connection with the embodiment of FIG. 4, there may be hole located in the bottom portion of the DMD. The hole may extend through the entire bottom portion of the DMD. Using the techniques described herein based on the electro wetting principles, the droplet may be positioned at a surface location over one of the control electrodes of the bottom portion at which the hole is located. The droplet may then be drawn into the fitting 654 and tube 656 connected thereto as described above with respect to the embodiment of FIG. 6.

Using the techniques herein, a liquid sample may be injected onto the surface of the bottom portion of the DMD. The sample may be aliquoted by manipulation of the electrical fields as described herein. The droplets formed may be manipulated by performing one or more processing operations for experimentation or other application for which the DMD is being utilized. The droplets may be moved, combined or merged, split, and the like, and stored on surfaces over one or more control electrodes. Using the techniques described herein, the product of the processing performed using the DMD may be further analyzed by transferring the droplets which are produced as a result of the processing to one or more other analysis instruments. The analysis instruments or devices may be used in connection with performing "off chip" analysis with respect to the DMD.

In connection the embodiments described herein used to interface the DMD to an MS device, the shape of the tip portion of the DMD is illustrated as having a pointed end. The end of the tip portion may be tapered to form a more rounded or blunt end. The geometry of the end of the tip portion may facilitate formation of the Taylor cone but the extent to which the end of the tip portion forms a pointed end may vary with embodiment.

Figure 8:
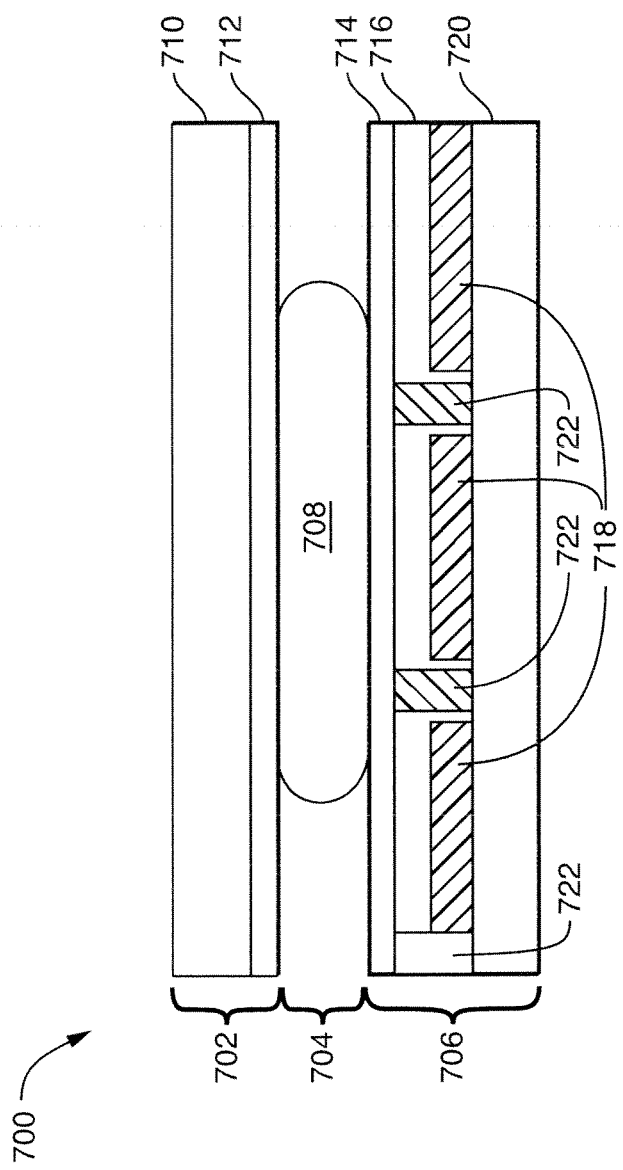
FIG. 8 is an example illustrating another embodiment of a DMD device that may be used in connection with the techniques herein with the reference and control electrodes incorporated in the bottom portion.

Referring to FIG. 8, shown is an example of another embodiment of the DMD. In this example 700, the DMD utilized a single-sided electrowetting microactuation mechanism as opposed to the two-sided electrowetting microactuation mechanism described in connection with FIG. 2B. The embodiment of the DMD of 700 is also described, for example, in U.S. Pat. No. 6,911,132, and US Patent Publication 2006/0194331, both of which are incorporated by reference herein. In the embodiment of 700, the reference electrode 722 and control electrodes 718 are co-planar and are both located in bottom portion 706. The control electrodes 718 are electrically insulated from the droplet 718 and from the reference electrode 722 by dielectric layer 716 and may be covered by hydrophobic coating 714. Although not illustrated in FIG. 8, the reference electrode may also be in electrical contact with the droplet. An embodiment may also have the reference electrode 722 covered by dielectric layer 716 and/or hydrophobic coating 714. Energizing a particular control electrode creates a gradient of surface tension that causes droplet D to move towards that electrode. By controlling the voltages applied to the control electrodes, the droplet may move in accordance with desired patterns and directions. Sequencing of the voltages applied to the control electrodes may be controlled as also described herein and known in the art, for example, in a predetermined manner using instructions executed by a processor. U.S. Pat. No. 6,911,132 and US Patent Publication 2006/0194331 describe additional details regarding the foregoing as illustrated in 700.

It should be noted that the control electrodes and reference electrodes of the example 700 may be arranged in a variety of different patterns and alignments. For example, the control electrodes may be included in an arrangement with rows of control electrodes forming a two dimensional grid as described above. The rows may be in vertical and/or horizontal alignment. As will be appreciated by those skilled in the art, other arrangements as well as shapes and sizes of the control electrodes and reference electrodes therebetween are possible for use in connection with the techniques herein.

In connection with the example 700 of FIG. 8, the reference electrode may extend to the tip portion of the DMD, have electrical contact with the droplet, and create the electrical field between the droplet and the MS inlet necessary for the establishment of a Taylor cone and an electrospray. Alternatively, the reference electrode may not extend into the tip portion of the DMD and may not contact the droplet but rather an external electrode is formed at the tip portion, for example, by deposition of a metallic layer and used to apply voltage to the droplet.

It should be noted that in an embodiment in which the DMD has the reference electrode in the bottom portion when using the arrangement of FIG. 4, an exposed portion of the reference electrode, rather than the control electrode N, may have a voltage applied thereto to create the Taylor cone and electrospray. In such an embodiment, the droplet in the tube 406 may have electrical contact with the reference electrode rather than the control electrode N as described above.

Figure 9:
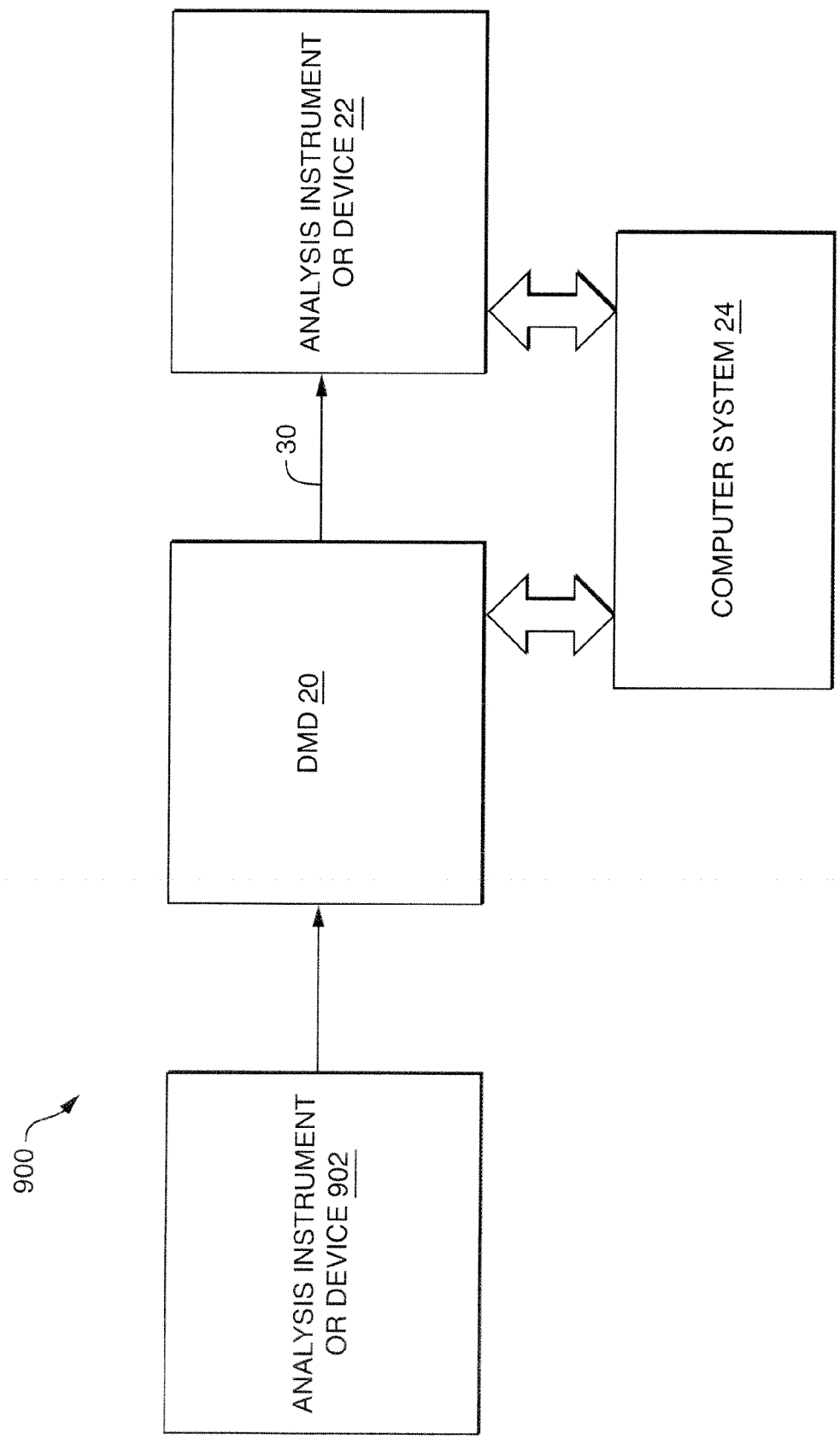
FIG. 9 is an example illustrating an embodiment using the techniques herein in which liquid is provided to the DMD from another device.

Referring to FIG. 9, shown is an example of an embodiment using the techniques herein in which fluid is provided to the DMD from another device. In the example 900, the elements 20, 22, 24 and 30 may be as described elsewhere herein in connection with FIG. 1. The example 900 also includes another analysis instrument or device 902 that may be used to provide fluid as an input to the DMD 20. The element 902 may represent a device or analysis instrument, such as a liquid chromatographic instrument, that provides a liquid sample to the DMD 20. Using the arrangement of FIG. 10, the DMD 20 may be used collect fractions of liquid sample from the eluent of an analytical instrument, such as the liquid chromatography instrument, formed into separate droplets. The DMD may be used to perform additional analyses and operations on the droplets. The product or result of the processing performed on the DMD may be transferred (as represented by element 30) to another analysis instrument or device 22, as described previously.

As a variation in connection with the components of FIG. 9 that may be used in connection with the techniques herein, an embodiment may omit elements 30 and 22. Such an embodiment may perform analysis and detection on the DMD rather than perform further analysis by transferring resulting droplets from the DMD to the analysis instrument or device 22 as may be done in connection with an embodiment including elements 30 and 22. Analysis that may be performed on the DMD may include any one of a variety of different types known in the art. In connection with the foregoing variation with respect to FIG. 9, it should be noted that droplets of different fluids are traditionally formed using different fluid reservoirs and inlet tubes. Using the foregoing variation of FIG. 9, an analytical instrument or device 22, such as an LC device, may be connected to a single inlet of a DMD and the DMD may be used to generate droplets of the eluent at different times thereby collecting fractions of the eluent of the analytical device 22. The collected fractions can be manipulated and analyzed further using the DMD. Detection can be on the DMD using, for example, laser-induced fluorescence, or the DMD can be connected to the inlet of another analytical device, as described above. It should also be noted that an embodiment may optionally process the droplets prior to performing detection. For example, prior to performing on-chip detection using the DMD, the droplets may be processed using a technique to enhance detection sensitivity.

It will be appreciated by those skilled in the art that an embodiment may also use other variations of the DMD than as described herein. The techniques described herein may also be used in connection with a DMD utilizing other techniques to create electrostatic forces to actuate the droplets based on other principles besides electrowetting. As an example, an embodiment utilizing the techniques herein may use dielectrophoretic (DEP) forces. As known in the art, DEP forces use a high-frequency AC electric field and rely on the difference of dielectric properties between the droplet and the surrounding medium. As another example, an embodiment may utilize electrostatic Coulomb forces.

It should be noted that although particular orientations between components are described herein, other orientations are possible.

As described herein, a computer system may be programmed using instructions or code executed by a processor to activate and deactivate selected ones of the control electrodes of the DMD to facilitate movement of the droplets. The instructions or code may also be used to automate other processing described herein, for example, such as control application of voltages to appropriate components in connection with generation of the electrical field causing formation of the Taylor cone and electrospray when used with an instrument performing mass spectrometry. The instructions or code may also be used in controlling other devices, such as a liquid chromatographic or other device that may be used in an embodiment in connection with the techniques herein. The instructions or code may stored on any one or more different forms of computer readable medium. As will be appreciated by those skilled in the art, the computer readable medium may have any one of a variety of different forms including volatile and nonvolatile, removable and non-removable media implemented in any method or technology for storage of information such as computer readable instructions, data structures, program modules or other data. Computer readable medium that may be used for storage for use with the techniques herein include, but are not limited to, RAM, ROM, EEPROM, flash memory or other memory technology, CD-ROM, (DVD) or other optical storage, magnetic cassettes, magnetic tape, magnetic disk storage or other magnetic storage devices, or any other medium which can be used to store the desired information and which can accessed by the processor.

While the invention has been disclosed in connection with preferred embodiments shown and described in detail, their modifications and improvements thereon will become readily apparent to those skilled in the art. Accordingly, the spirit and scope of the present invention should be limited only by the following claims.

What is claimed is:

1. A method of analyzing a droplet comprising:
   forming one or more droplets of a sample on a surface of a digital microfluidic device;
   manipulating said one or more droplets of the sample to perform processing using said one or more droplets of the sample generating one or more resulting droplets; and
   transferring said one or more resulting droplets from said digital microfluidic device to another device for analysis, wherein said another device performs mass spectrometry, wherein said digital microfluidic device interfaces with said another device using a tube coupled to the digital microfluidic device, wherein the tube is perpendicular to a plane containing said digital microfluidic device and wherein the digital microfluidic device includes a hole formed through a bottom portion of the digital microfluidic device and the tube is connected to the hole in the bottom portion, wherein said tube is electrically conductive providing electrical contact between a control electrode in said bottom portion of said microfluidic device and a tip of said tube, wherein the tip of the tube is formed at a tapered end that extends in a direction substantially perpendicular to the plane containing the digital microfluidic device, and wherein the method further includes:
   creating an electrical field by applying a voltage to said control electrode in said bottom portion of said digital microfluidic device, said electrical field being sufficient to cause formation of a Taylor cone at said tip of said tube and electrospray.

2. The method of claim 1, wherein the bottom portion includes a plurality of control electrodes and said manipulating is performed by controlling voltages associated with the plurality of control electrodes located in the bottom portion of said digital microfluidic device and said one or more droplets of the sample are located on a surface of said bottom portion over said plurality of control electrodes.

3. The method of claim 1, wherein said digital microfluidic device includes a top portion, said one or more droplets of the sample are positioned on a surface of said bottom portion and between said top portion and said bottom portion.

4. The method of claim 3, wherein the top portion includes a substrate layer with a reference electrode embedded therein or formed thereon.

5. The method of claim 4, wherein the top portion includes a hydrophobic insulation layer covering the reference electrode.

6. The method of claim 4, wherein the bottom portion includes a plurality of control electrodes including said control electrode and wherein said plurality of control electrodes are covered by a hydrophobic insulation layer.

7. The method of claim 1, wherein applying said voltage at said control electrode in said bottom portion causes a first droplet of said one or more resulting droplets to move to a location over said control electrode at which said tube is connected, said first droplet moving from said location on said digital microfluidic device through the hole in said bottom portion at said location, said first droplet flowing through said tube to said tip of said tube containing an opening therein.

8. The method of claim 7, wherein said tube is made of an electrically conductive material.

9. The method of claim 1, wherein said tube has an inner hydrophilic surface.

10. The method of claim 1, wherein said manipulating includes processing to perform a chemical reaction.

11. The method of claim 1, further comprising:
  providing said one or more droplets of the sample used on the surface of a digital microfluidic device from an analysis instrument.

12. The method of claim 11, wherein said analysis instrument is a liquid chromatographic instrument.

13. The method of claim 1, wherein inside surfaces of said tube are hydrophilic.

* * * * *